United States Patent
Morris et al.

(10) Patent No.: US 9,314,572 B2
(45) Date of Patent: Apr. 19, 2016

(54) CONTROLLING DRUG DELIVERY TRANSITIONS

(71) Applicant: Medtronic, Inc., Minneapolis, MN (US)

(72) Inventors: Mary M. Morris, Shoreview, MN (US); Mark A. Bellrichard, Champlin, MN (US); Robert Garfield, Cincinnati, OH (US); Daniel Gelfman, Golden Valley, MN (US); Lu Wang, Minneapolis, MN (US); Michael W. Kimmel, Edina, MN (US); Karen J. Kleckner, New Brighton, MN (US); Brian W. Ball, Maple Grove, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 152 days.

(21) Appl. No.: 14/077,069

(22) Filed: Nov. 11, 2013

(65) Prior Publication Data

US 2015/0133886 A1    May 14, 2015

(51) Int. Cl.
     *A61M 5/172*      (2006.01)
     *A61M 5/142*      (2006.01)
     *G06F 19/00*      (2011.01)
(Continued)

(52) U.S. Cl.
CPC ........... *A61M 5/172* (2013.01); *G06F 19/3468* (2013.01); *A61M 5/142* (2013.01); *A61M 5/1407* (2013.01); *A61M 5/14244* (2013.01); *A61M 5/168* (2013.01); *A61M 5/16827* (2013.01);
(Continued)

(58) Field of Classification Search
CPC ... A61M 5/172; A61M 5/1407; A61M 5/142; A61M 5/14244; A61M 5/168; A61M 5/16827; A61M 5/16886; A61M 2005/3379; G06F 19/3468

See application file for complete search history.

(56) References Cited

U.S. PATENT DOCUMENTS

| 8,162,888 | B2 | 4/2012 | Kalpin |
| 8,246,573 | B2 | 8/2012 | Ali et al. |

(Continued)

FOREIGN PATENT DOCUMENTS

| EP | 0302752 A2 | 2/1989 |
| WO | 03082380 A1 | 10/2003 |
| WO | 2005084273 A2 | 9/2005 |

OTHER PUBLICATIONS

Baiyasi, S., Constan, K., Dewey, E., & Hersh, L. (2001). Math for nursing and allied health. Retrieved May 19, 2015.*
(Continued)

*Primary Examiner* — Kami A Bosworth
*Assistant Examiner* — Nilay Shah
(74) *Attorney, Agent, or Firm* — Shumaker & Sieffert, P.A.

(57) ABSTRACT

Devices, systems, and techniques for transitioning between different drug delivery sources or different drug concentrations may account for diffusion and mixing of drug within the fluid. In one example, a method may include determining a flow rate for a fluid to be delivered to a patient via a drug pump and a catheter in fluid communication with a reservoir of the drug pump. The fluid includes a drug. The method also includes determining a concentration profile of the drug delivered via the catheter, wherein the concentration profile identifies a volume of delivered fluid needed to achieve a target transition dose of the drug. The method further includes determining, by a processor and based on the flow rate and the concentration profile, an initial delivery period required to achieve the target transition dose by delivering the fluid at the flow rate.

24 Claims, 12 Drawing Sheets

(51) Int. Cl.
*A61M 5/14* (2006.01)
*A61M 5/168* (2006.01)

(52) U.S. Cl.
CPC .... *A61M 2205/3379* (2013.01); *A61M 2205/52* (2013.01)

(56) References Cited

U.S. PATENT DOCUMENTS

| | | | |
|---|---|---|---|
| 8,348,884 B2 | 1/2013 | Hildebrand et al. | |
| 8,352,043 B2 | 1/2013 | Goetz et al. | |
| 8,444,609 B2 | 5/2013 | Christenson et al. | |
| 2003/0216682 A1* | 11/2003 | Junker | 604/65 |
| 2006/0041222 A1 | 2/2006 | Dewing et al. | |
| 2006/0041223 A1 | 2/2006 | Dewing et al. | |
| 2006/0041287 A1 | 2/2006 | Dewing et al. | |
| 2006/0041288 A1 | 2/2006 | Dewing et al. | |
| 2006/0160900 A1* | 7/2006 | Hildebrand et al. | 514/561 |
| 2007/0255236 A1 | 11/2007 | Christenson et al. | |
| 2009/0137980 A1 | 5/2009 | Ali | |
| 2009/0137987 A1 | 5/2009 | Ali | |
| 2010/0010646 A1 | 1/2010 | Drew et al. | |
| 2010/0185181 A1 | 7/2010 | Alme et al. | |
| 2010/0185182 A1* | 7/2010 | Alme et al. | 604/891.1 |
| 2010/0185183 A1 | 7/2010 | Alme et al. | |
| 2010/0274221 A1 | 10/2010 | Sigg et al. | |
| 2010/0312230 A1 | 12/2010 | Ullestad et al. | |
| 2011/0144540 A1 | 6/2011 | Shen et al. | |
| 2011/0166522 A1 | 7/2011 | Haase et al. | |
| 2011/0257591 A1 | 10/2011 | Nelson Konen et al. | |
| 2011/0257798 A1 | 10/2011 | Ali et al. | |
| 2011/0264006 A1 | 10/2011 | Ali et al. | |
| 2011/0264034 A1 | 10/2011 | Roberts et al. | |
| 2012/0053514 A1 | 3/2012 | Robinson et al. | |
| 2012/0053562 A1 | 3/2012 | Haase | |
| 2012/0109099 A1 | 5/2012 | Rogers et al. | |
| 2012/0209241 A1 | 8/2012 | Drew | |
| 2012/0220528 A1 | 8/2012 | Van Antwerp et al. | |
| 2012/0277155 A1 | 11/2012 | VanAntwerp et al. | |
| 2012/0277716 A1 | 11/2012 | Ali et al. | |
| 2012/0277717 A1 | 11/2012 | Ali et al. | |
| 2013/0041418 A1 | 2/2013 | Rubin et al. | |

OTHER PUBLICATIONS

Baiyasi et al., "Math for Nursing and Allied Health," Teaching/Learning Center, Delta College, Jan. 2001, 21 pp.

International Search Report and Written Opinion from International Application No. PCT/US2014/063507, dated Mar. 11, 2015, 11 pages.

* cited by examiner

CONTROLLING DRUG DELIVERY TRANSITIONS

TECHNICAL FIELD

The present disclosure relates to medical devices and, more particularly, fluid delivery devices.

BACKGROUND

Implantable fluid delivery devices may be used to treat a number of physiological, psychological, and emotional conditions, including chronic pain, tremor, Parkinson's disease, epilepsy, cancer, diabetes, urinary or fecal incontinence, sexual dysfunction, obesity, spasticity, or gastroparesis. For some medical conditions, an implantable fluid delivery device provides the best, and in some cases the only, therapy to restore a patient to a more healthful condition.

An implantable fluid delivery device typically provides a patient with a programmable dosage or infusion of a drug or other therapeutic agent. A fluid delivery device typically can include a reservoir for storing the therapeutic agent, a fill port, a pumping mechanism to pump the therapeutic agent from the reservoir, a catheter to transport the therapeutic agent from the reservoir to a patient's anatomy, and electronics to control the pumping mechanism.

SUMMARY

In general, the disclosure relates to systems and methods for transitioning between different deliveries of drugs. The transition may include changing between different drug delivery sources (e.g., external and implanted drug pumps), changing between different concentrations of a drug, or even changing the type of one or more drugs being delivered to a patient. A system may obtain a flow rate and concentration profile of a drug to be delivered to a patient. The concentration profile may indicate a volume of fluid that needs to be delivered from a catheter in order to reach a target transition dose of the drug. The target transition dose is generally greater than or less than the target prescribed dosage. The system may then determine an initial delivery period required to achieve the target transition dose before subsequent action is taken, such as removing an external drug pump catheter or changing the flow rate to a new flow rate needed to achieve the target prescribed dosage.

In one example, the disclosure is directed to a method that includes determining a flow rate for a fluid to be delivered to a patient via a drug pump and a catheter in fluid communication with a reservoir of the drug pump, wherein the fluid comprises a therapeutic agent, determining a concentration profile of the therapeutic agent delivered via the catheter, wherein the concentration profile identifies a volume of fluid deliverable by the drug pump and needed to achieve a target transition dose of the therapeutic agent, and determining, by a processor and based on the flow rate and the concentration profile, an initial delivery period required to achieve the target transition dose by delivering the fluid at the flow rate.

In another example, the disclosure is directed to a system comprising one or more processors configured to determine a flow rate for a fluid to be delivered to a patient via a drug pump and a catheter in fluid communication with a reservoir of the drug pump, wherein the fluid comprises a therapeutic agent, determine a concentration profile of the therapeutic agent delivered via the catheter, wherein the concentration profile identifies a volume of fluid deliverable by the drug pump and needed to achieve a target transition dose of the therapeutic agent, and determine, based on the flow rate and the concentration profile, an initial delivery period required to achieve the target transition dose by delivering the fluid at the flow rate.

In another example, the disclosure is directed to a system that includes means for determining a flow rate for a fluid to be delivered to a patient via a drug pump and a catheter in fluid communication with a reservoir of the drug pump, wherein the fluid comprises a therapeutic agent, means for determining a concentration profile of the therapeutic agent delivered via the catheter, wherein the concentration profile identifies a volume of fluid deliverable by the drug pump and needed to achieve a target transition dose of the therapeutic agent, and means for determining, based on the flow rate and the concentration profile, an initial delivery period required to achieve the target transition dose by delivering the fluid at the flow rate.

In another example, the disclosure is directed to a computer-readable storage medium containing instructions. The instructions cause a programmable processor to determine a flow rate for a fluid to be delivered to a patient via a drug pump and a catheter in fluid communication with a reservoir of the drug pump, wherein the fluid comprises a therapeutic agent, determine a concentration profile of the therapeutic agent delivered via the catheter, wherein the concentration profile identifies a volume of fluid deliverable by the drug pump and needed to achieve a target transition dose of the therapeutic agent, and determine, based on the flow rate and the concentration profile, an initial delivery period required to achieve the target transition dose by delivering the fluid at the flow rate.

The details of one or more examples of the invention are set forth in the accompanying drawings and the description below. Other features, objects, and advantages will be apparent from the description and drawings, and from the claims.

DETAILED DESCRIPTION

Figure 1:
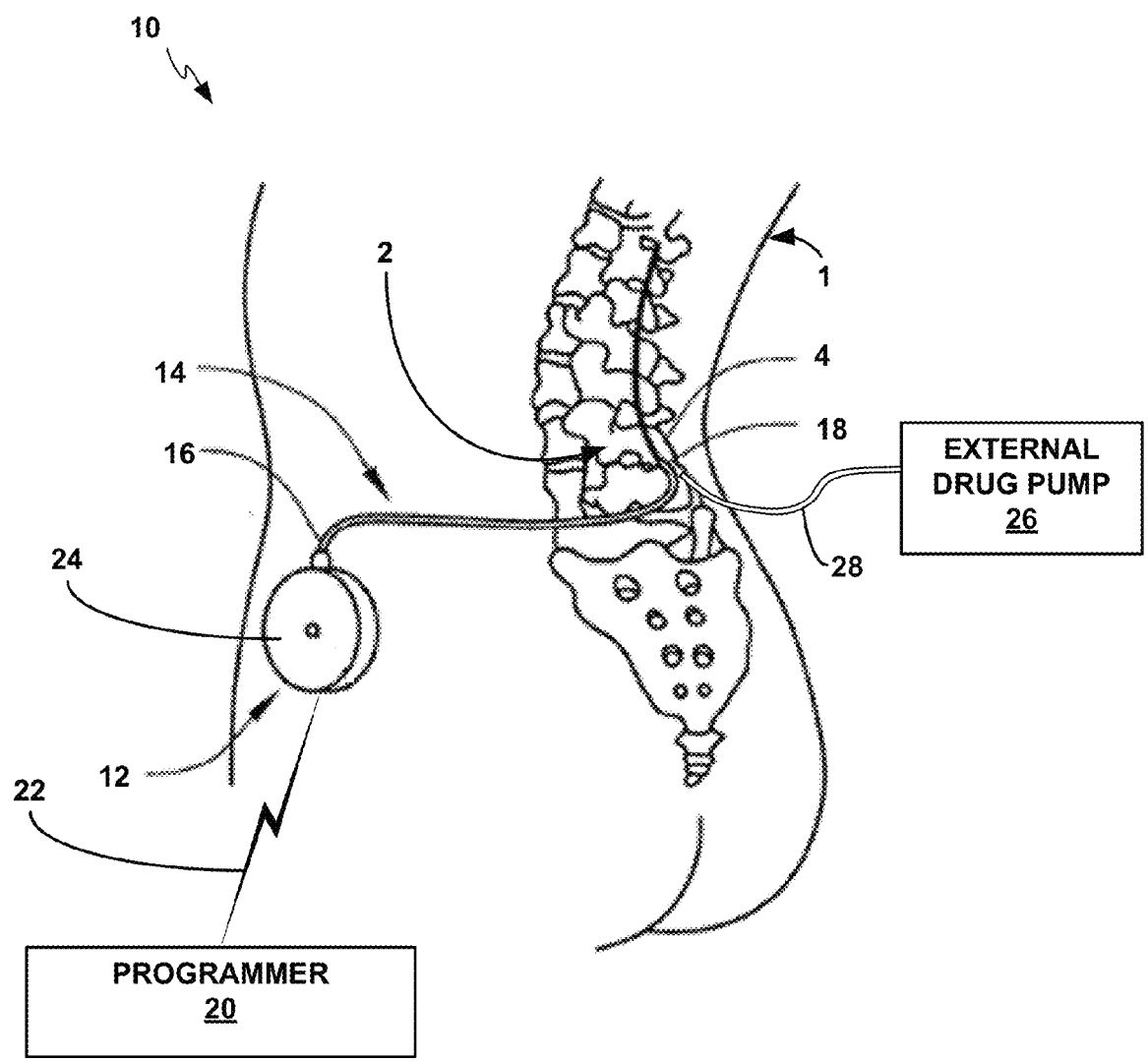
FIG. 1 is a conceptual diagram illustrating an example of a fluid delivery system, which includes an implantable medical device (IMD), e.g., a fluid delivery device with a medical pump, and an external drug pump.

The disclosure describes example systems and methods for transitioning between different deliveries of drugs (or other therapeutic fluids) by a therapeutic agent delivery system (also referred to herein as a "drug delivery system" or a "fluid delivery system"). The transition may include changing between different drug delivery sources (e.g., external and implanted drug pumps), changing between different concentrations of a drug, changing the type of one or more drugs being delivered to a patient, or even beginning drug delivery. Timing of the delivery of a new drug and/or termination of the previous drug may affect the overall dose the patient receives.

Transition times used to change between different deliveries of a drug may be calculated from a location in which a new drug is added to a fluid path of a drug delivery system. For example, the time for moving a drug from a reservoir of a fluid delivery device to a patient can be based on the dead space volume (e.g., the volume within the pump and the catheter downstream from the reservoir) and the flow rate applied. The dead space volume, however, may include another fluid (e.g., saline or drug of a different concentration than that of the drug in the reservoir). Therefore, as the drug moves through a fluid path including a catheter, the drug may diffuse or otherwise mix forward into the adjacent fluid in the catheter. In this manner, the fluid path may include three fluids, a downstream first fluid (e.g., an inert fluid or a fluid with a therapeutic agent at a first concentration), an upstream second fluid (e.g., a fluid with a therapeutic agent at a second concentration), and a mixed fluid in the fluid path between the first and second fluids and including a mixture of the first and second fluids.

As described herein, systems and techniques may be employed to estimate a relatively accurate total dosing of a drug when drug delivery is started or modified. This accurate dosing may be determined based on fluid mixing prior to exiting out of a catheter (and delivered into tissue of the patient) and allow a clinician to deliver a target transition dose during the transition to manage potential overdosing (i.e., dosing greater than a target prescribed dose) and underdosing (i.e., dosing less than a target prescribed dose) of the patient. The system may obtain a flow rate and concentration profile of the drug to be delivered to the patient. The concentration profile may indicate a volume of fluid that needs to be delivered from a catheter in order to reach a target transition dose of the drug. This concentration profile may account for drug diffusion or mixing of the drug in another fluid prior to the drug reaching the patient and may be determined experimentally or calculated by modeling the system.

The target transition dose is generally greater than or less than the target prescribed dosage for the patient. The system may then determine an initial delivery period required to achieve the target transition dose before subsequent action is taken. For example, upon expiration of the initial delivery period, the system may prompt a clinician to remove an external drug pump catheter (e.g., after a prime bolus and a portion of mixed fluid has been delivered) or control an adjustment of the flow rate to a new flow rate needed to achieve the target prescribed dosage with the new drug (e.g., after a bridge bolus and portion of mixed fluid has been delivered). In this manner, the target transition dose may be selected by the clinician such that an appropriate initial delivery period may be determined for the prime bolus or the bridge bolus and the appropriate additional volume of mixed fluid. In some examples, the system may also be configured to present information (e.g., data and/or a graph) illustrating the total dosing of the patient over time during these drug delivery transitions. A prime bolus may include a volume of inert fluid delivered out from a newly implanted IMD and/or catheter prior to a portion of mixed fluid that includes a therapeutic agent stored in a reservoir of the IMD. A bridge bolus may include a volume of a first fluid having a first concentration of a therapeutic agent delivered prior to a mixture between the first fluid and a second fluid including the therapeutic agent at a different concentration or a different therapeutic agent. In this manner, a bridge bolus may be delivered during a transition between two different concentrations of a therapeutic agent or between two different therapeutic agents, such as when the reservoir of an IMD is refilled with a new therapeutic agent.

FIG. 1 is a conceptual diagram illustrating an example of a system 10, which includes implantable medical device (IMD) 12, e.g., a fluid delivery device with a medical pump, and external drug pump 26. As shown in FIG. 1, IMD 12 may be configured to deliver a therapeutic agent, such as a pharmaceutical agent, for example a drug, insulin, pain relieving agent, anti-inflammatory agent, gene therapy agent, or the like, to a target site 2 within a patient 1. While a drug is primarily referred to herein, in other examples, the devices, systems, and techniques described herein can be used with other therapeutic agents.

The therapeutic agent (e.g., a drug) is delivered via a catheter 14 that is coupled to IMD 12. Catheter 14 may comprise a plurality of catheter segments, or catheter 14 may be a unitary catheter. In the example shown in FIG. 1, target site 2 is proximate to spinal cord 4 of patient 1. A proximal end 16 of catheter 14 is coupled to IMD 12 while a distal end 18 of catheter 14 is positioned proximate target site 2.

System 10 may also include an external programmer 20 that communicates with IMD 12 as needed, such as to provide or retrieve therapy information or therapy parameters associated with therapy delivery. For example, external programmer 20 may be configured to turn IMD 12 on or off, to deliver the initial therapy parameters for patient 1, to modify the therapy parameters, and so forth. In one example, external programmer 20 communicates with IMD 12 wirelessly 22, as shown in FIG. 1.

Although patient 1 is generally referred to as a human patient in the present disclosure, system 10 can be used with other mammalian or non-mammalian patients. IMD 12 may be employed to treat, manage or otherwise control various conditions or disorders of patient 1, including, e.g., pain (e.g., chronic pain, post-operative pain or peripheral and localized pain), tremor, movement disorders (e.g., Parkinson's disease), diabetes, epilepsy, neuralgia, chronic migraines, urinary or fecal incontinence, sexual dysfunction, obesity, gastroparesis, cancer, mood disorders, or other disorders.

IMD 12 may be configured to deliver one or more therapeutic agents, alone or in combination with other therapies, including, e.g., electrical stimulation. For example, in some cases, a medical pump may deliver one or more pain-relieving drugs to patients with chronic pain, insulin to a patient with diabetes, or other fluids to patients with different disorders. IMD 12 may be implanted in patient 1 for chronic or temporary therapy delivery.

IMD 12 includes an outer housing 24 that is constructed of a biocompatible material that resists corrosion and degradation from bodily fluids, such as titanium or biologically inert polymers. IMD 12 may be implanted within a subcutaneous pocket close to target site 2. For example, as shown in FIG. 1, IMD 12 may be implanted within the abdomen of patient 1 close to the position along spinal cord 4 where target site 2 is located. In other examples, IMD 12 may be implanted within other suitable sites within patient 1, which may depend, for example, on where target site 2 is located within patient 1, and the ease of implanting IMD 12 within suitable locations near target site 2.

Catheter 14 may be coupled to IMD 12 either directly or with the aid of a catheter extension (not shown). In the example shown in FIG. 1, catheter 14 traverses from the implant site of IMD 12 to target site 2 proximate to spinal cord 4. Catheter 14 is positioned such that one or more fluid delivery outlets of catheter 14 are proximate to one or more locations within patient 1. In the example shown in FIG. 1, IMD 12 delivers a therapeutic agent to one or more locations at target site 2 proximate to spinal cord 4 with the aid of catheter 14. For example, IMD 12 may be configured for intrathecal drug delivery into the intrathecal space or epidural space surrounding spinal cord 4.

In some examples, multiple catheters may be coupled to IMD 12 to target the same or different tissue or nerve sites within patient 1. Thus, although a single catheter 14 is shown connected to IMD 12 in FIG. 1, in other examples, system 10 may include multiple catheters or catheter 14 may define multiple lumens for delivering different therapeutic agents to patient 1 or for delivering a therapeutic agent to different tissue sites within patient 1. Accordingly, in some examples, IMD 12 may include a plurality of reservoirs for storing more than one type of therapeutic agent. In some examples, IMD 12 may include a single long tube that contains the therapeutic agent in place of a reservoir. However, for ease of description, an IMD 12 including a single reservoir is primarily discussed herein with reference to the example of FIG. 1.

IMD 12 may deliver one or more therapeutic agents to patient 1 according to one or more therapy programs. Example therapeutic agents that IMD 12 may be configured to deliver include insulin, morphine, hydromorphone, bupivacaine, clonidine, other analgesics, genetic agents, antibiotics, nutritional fluids, analgesics, hormones or hormonal drugs, gene therapy drugs, anticoagulants, cardiovascular medications or chemotherapeutics. A therapy program, generally speaking, may set forth different therapy parameters, such as a therapy schedule specifying programmed doses, dose rates for the programmed doses, and specific times to deliver the programmed doses.

The therapy programs may be a part of a program group for therapy, wherein the group includes a plurality of constituent therapy programs and/or therapy schedules. In some examples, IMD 12 may be configured to deliver a therapeutic agent to patient 1 according to different therapy programs on a selective basis. IMD 12 may include a memory to store one or more therapy programs, instructions defining the extent to which patient 1 may adjust therapy parameters, switch between therapy programs, or undertake other therapy adjustments. Patient 1 may select and/or generate additional therapy programs for use by IMD 12 via external programmer 20 at any time during therapy or as designated by the clinician.

In one example, programmer 20 is an external computing device that is configured to communicate with IMD 12, such as via a wireless communications link 22. For example, programmer 20 may be a clinician programmer that the clinician uses to communicate with IMD 12, such as retrieving data and providing instructions regarding delivery of drugs to patient 1. Alternatively, programmer 20 may be a patient programmer that allows patient 1 to view and modify therapy parameters. A clinician programmer may include additional or alternative programming features, relative to a patient programmer, which may have more limited features such as limited programming capability. For example, more complex or sensitive tasks may only be allowed by the clinician programmer to prevent patient 1 from making undesired changes to the operation of IMD 12.

Programmer 20 may be a hand-held computing device that includes a display viewable by the user and a user input mechanism that can be used to provide input to programmer 20. For example, programmer 20 may include a display screen (e.g., a liquid crystal display or a light emitting diode display) that presents information to the user. In addition, programmer 20 may include a keypad, buttons, a peripheral pointing device, touch screen, voice recognition, or another input mechanism that allows the user to navigate through the user interface of programmer 20 and provide input.

In other examples, rather than being a handheld computing device or a dedicated computing device, programmer 20 may be a larger workstation or a separate application within another multi-function device. For example, the multi-function device may be a cellular phone, personal computer, laptop, workstation computer, or personal digital assistant that can be configured to an application to simulate programmer 20. Alternatively, a notebook computer, tablet computer, or other personal computer may execute an application to function as programmer 20, e.g., with a wireless adapter connected to the personal computer for communicating with IMD 12.

When programmer 20 is configured for use by the clinician, programmer 20 may be used to transmit initial programming information to IMD 12. This initial information may include hardware information for system 10 such as the type of catheter 14, the position of catheter 14 within patient 1, the type of therapeutic agent(s) delivered by IMD 12, a baseline orientation of at least a portion of IMD 12 relative to a reference point, therapy parameters of therapy programs stored within IMD 12 or within programmer 20, and any other information the clinician desires to program into IMD 12.

A clinician uses programmer 20 to program IMD 12 with one or more therapy programs that define the therapy delivered by IMD 12. During a programming session, the clinician may determine one or more therapy programs, which may include one or more therapy schedules, programmed doses, dose rates of the programmed doses, and specific times to deliver the programmed doses that may provide effective therapy to patient 1. Patient 1 may provide feedback to the clinician as to the efficacy of a specific therapy program being evaluated or desired modifications to the therapy program. Once the clinician has identified one or more programs that may be beneficial to patient 1, patient 1 may continue the evaluation process and determine which dosing program or therapy schedule best alleviates the condition of patient 1 or otherwise provides efficacious therapy to patient 1.

In some cases, programmer 20 may be configured for use by patient 1. When configured as a patient programmer, programmer 20 may have limited functionality in order to prevent patient 1 from altering critical functions or applications that may be detrimental to patient 1. In this manner, programmer 20 may only allow patient 1 to adjust certain therapy parameters or set an available range for a particular therapy parameter. In some cases, a patient programmer may permit the patient to control IMD 12 to deliver a supplemental, patient bolus, if permitted by the applicable therapy program administered by the IMD, e.g., if delivery of a patient bolus would not violate a lockout interval or maximum dosage limit. Programmer 20 may also provide an indication to patient 1 when therapy is being delivered or when IMD 12 needs to be refilled or when the power source within programmer 20 or IMD 12 needs to be replaced or recharged. The reservoir of IMD 12 may be refilled with the same drug with same concentration, the same drug with a different concentration, or a different drug. IMD 12 may provide a bridge bolus when transitioning between difference concentrations or different drugs, as described herein.

Whether programmer 20 is configured for clinician or patient use, programmer 20 may communicate to IMD 12 or any other computing device via wireless communication. Programmer 20, for example, may communicate via wireless communication link 22 with IMD 12 using any of a number of radio frequency (RF) telemetry techniques. Programmer 20 may also communicate with another programmer or computing device via a wired or wireless connection using any of a variety of local wireless communication techniques, such as RF communication according to one or more specification sets, such as the Medical Implant Communication Service (MICS) specification set, Medical Implant Telemetry System (MITS), Medical Data Service (MEDS), 802.11, or Bluetooth specification sets, infrared (IR) communication according to the IRDA specification set, or other standard or proprietary telemetry protocols. Programmer 20 may also communicate with another programmer or computing device via exchange of removable media, such as magnetic or optical disks, or memory cards or sticks. Further, programmer 20 may communicate with IMD 12 and another programmer via remote telemetry techniques, communicating via a local area network (LAN), wide area network (WAN), public switched telephone network (PSTN), or cellular telephone network, for example.

In addition to IMD 12, external drug pump 26 may be used to deliver drug to patient 1 at or near target site 2 via catheter 28. System 10 including only one catheter 28 will be primarily described herein, but, in other examples, system 10 may include two or more catheters implanted within patient 1 and fluidically coupled to external drug pump 26. External drug pump 26 may include a drug reservoir, one or more processors, memory, and other components for controlling delivery of drug to patient 1. In some examples, programmer 20 may be configured to receive data from external drug pump 26 and/or transmit instructions for controlling external drug pump 26. External programmer 26 may also include a user interface (e.g., a display device and/or input device) to present information to a user and receive instructions from a user such as starting and stopping drug delivery.

Patient 1 may generally receive drug from only external drug pump 26 or IMD 12. However, patient 1 may receive a drug (e.g., the drug in fluid from respective sources) from both external drug pump 26 and IMD 12 during one or more periods of time. For example, patient 1 may receive a drug from external drug pump 26 first, before IMD 12 is implanted. Once IMD 12 is implanted within patient 1 and catheter 14 is positioned at target site 2, a clinician may transition drug delivery from external drug pump 26 to IMD 12 before external drug pump 26 is turned off and catheter 28 is explanted from patient 1. IMD 12 may be controlled to deliver a prime bolus to patient 1 while external drug pump 26 continues to deliver drug to patient 1. In some examples, during this transition period that may include delivery of the prime bolus by IMD 12, drug may be delivered to patient 1 simultaneously from external drug pump 26 and IMD 12 to minimize the time and amount by which patient 1 is underdosed and minimize the time and amount by which patient 1 is overdosed during this simultaneous delivery.

As described herein, system 10 may utilize a flow rate and concentration profile of a drug to determine an initial delivery period for the drug delivered by IMD 12, external drug pump 26, or both IMD 12 and external drug pump 26. Upon expiration of the initial delivery period, system 10 may facilitate a change in drug delivery (e.g., termination of delivery via external drug pump 26 or switching from one flow rate to a different flow rate of the drug). The initial delivery period may thus be determined to achieve a target transition dose of a drug for patient 1 that may minimize both overdosing and underdosing during the transition between drug delivery sources and/or concentrations of the drug.

One or more of IMD 12, programmer 20, or external drug pump 26 may include one or more processors configured to perform various functions related to achieving a target transition dose. In one example, one or more processors of programmer 20 may be configured to determine a flow rate for a fluid to be delivered to patient 1 via IMD 12 and catheter 14 in fluid communication with a reservoir of IMD 12. The fluid may include at least a portion of the drug to be delivered to patient 1. The one or more processors of programmer 20 may also obtain a concentration profile of the drug delivered via catheter 14. The concentration profile may identify a volume of fluid delivered over time needed to achieve a target transition dose of the drug at patient 1. Programmer 20 may then determine, based on the flow rate and the concentration profile, an initial delivery period required to achieve the target transition dose by delivering the fluid at the flow rate. As described herein, the concentration profile may be obtained from memory, generated by one or more of IMD 12, programmer 20, and/or extrapolated from another previously stored concentration profile.

The concentration profile of the drug may represent the differential drug concentration of the fluid within catheter 14. When two fluids come in contact with each other, the boundary between the fluids may not remain highly defined. Instead, respective portions of the two fluids may mix with each other or undergo some diffusion at the boundary. The result is a gradient, or profile, that represents the interface between the two fluids. In other words, there is some volume of fluid at the interface that contains a portion of both fluids. The concentration profile of the drug within this interface can indicate the concentration of the drug at various positions within the fluid.

In the example of a newly implanted IMD 12 and catheter 14, the reservoir of IMD 12 may contain the drug to be delivered to patient 1 and catheter 14 may be filled with a priming fluid that is inert, such as saline, water, or other physiologically inert fluid. At the boundary between the catheter fluid and the drug in the reservoir of IMD 12, some drug mixes with the priming fluid. The concentration profile may represent, define, or estimate the mixing that occurs at this boundary. In the example of refilling an implanted IMD 12 with a drug of a different concentration than the previous concentration delivered to patient 1, a drug with the previous concentration may still be within catheter 14 whereas the new concentration of the drug is contained within the reservoir. The interface between the fluids of each concentration may contain mixing of the concentrations such that the concentration of drug at the interface is of some gradient between the two concentrations. The concentration profile of the drug may represent the mixing of drug at this interface to estimate the actual concentration for a given volume of the fluid at the interface.

System 10 can include a memory (e.g., within programmer 20, IMD 12, or external drug pump), or be communicatively coupled to a remote memory, that stores concentration profiles for one or more different combinations of fluids (e.g., two drugs, a drug and saline, and the like). A processor of system 10 can determine the concentration profile by retrieving the profile from the memory, or by determining the concentration profile based on one or more factors. Example factors may include the diffusion coefficient of the drug (e.g., diffusion of the drug within the fluid of catheter 14), the diffusion coefficient of any other liquids, viscosity of the fluid, the temperature of the fluid (e.g., drug and/or liquid), flow rate of fluid through the fluid path including catheter 14, the diameter of catheter 14, the length of catheter 14, pressure within catheter 14, and/or any other factors that may affect the concentration profile. Other factors affecting the concentration profile may include how the different fluids are added to the fluid path and where the interface is located within the fluid path. For example, interface locations may be where catheter port 46 (shown in FIG. 2) meets catheter 14 or where reservoir 30 meets internal passage 44. Upstream locations may allow greater time for mixing and different diameters in the fluid path may affect how large the of an area the two fluids contact each other. For example, system 10 or another device may automatically calculate the concentration profile based on one or more of the factors above.

In some examples, the concentration profile of a drug may be determined experimentally and stored in a memory for later retrieval by a processor of system 10. The concentration profile may be experimentally determined for each specific catheter length and/or diameter. In some examples, a concentration profile may be experimentally determined for one or more given factors and extrapolated to fit different situations.

The target transition dose may be the dose of one or more drugs selected for patient 1 for the purpose of minimizing overdosing and/or underdosing patient 1 during the transition of drug delivery (e.g., between two different drugs or two different concentrations of a drug). The target transition dose may be represented as a percentage of the target prescribed dose of a drug for patient 1. The target transition dose may thus be a dose of the drug delivered to patient 1 from the combination of delivery of drug from different sources or with different concentrations. As examples, the target transition dose may be achieved from 100 percent of one drug source or one drug concentration and a portion of another drug source of another drug concentration. In some examples, the target transition dose as a maximum or minimum deviation from the target prescribed dose of one or more drugs. The transition concentration of the drug within the mixed fluid (e.g., the concentration of the drug within catheter 14 that is a mixture of two adjacent fluids within the fluid path) during the initial delivery period may be different than the reservoir concentration of the drug stored within the reservoir of IMD 12. The transition concentration may thus reflect the concentration at a given location within the mixed fluid between upstream and downstream fluids.

In some examples, the target transition dose of the drug is different than a target prescribed dose of the drug. This difference may be selected to allow the actual drug dose to drift back to the target prescribed dose during the transition period. For example, the target transition dose may be between 50 percent and 150 percent of the target prescribed dose. However, the target transition dose may be less than 50 percent or greater than 150 percent in other examples. In one example, the target transition dose may be 120 percent of the target prescribed dose. During the transition period, system 10 may deliver the drug such that the actual patient dose rises to 120 percent of the target prescribed dose. The initial delivery period may be determined by system 10 such that the initial delivery period expires when the actual patient dose reaches the target transition dose (e.g., 120 percent of the target prescribed dose).

In one example, the target transition dose may be selected by a clinician and input to programmer 20, external drug pump 26, or another user interface device. In other words, programmer 20, external drug pump 26, and or another user interface device may include a user interface configured to receive the input from the user. A clinician may, for example, select the target transition dose based on one or more of the conditions of patient 1, the type of drug delivered, or to be delivered, to patient 1, the type of transition for the drug (e.g., prime bolus or bridge bolus), historical data, or any other factor. In other examples, one or more devices of system 10 may automatically select the target transition dose, e.g., based on one or more factors, such as the type of drug, one or more conditions of patient 1, the type of transition (e.g., prime bolus or bridge bolus), and previously used target transition doses. In some examples, system 10 may receive the target transition dose from a networked server via a network.

One or more devices of system 10 may then use the flow rate, the concentration profile, and target transition dose of the drug to determine an initial delivery period. The initial delivery period may thus represent the time at which a prime bolus and subsequent portion of the mixed fluid or a bridge bolus and subsequent portion of the mixed fluid is complete and delivery should switch to the prescribed second delivery parameters of the drug to be delivered to the patient. In the example of a prime bolus as described in FIG. 1, one or more drugs may be delivered to patient 1 from both external drug pump 26 and IMD 12 during the initial delivery period. Upon expiration of the initial delivery period, delivery of drug from external drug pump 26 may terminate while drug delivery from IMD 12 continues. In the example of a bridge bolus in which a different concentration of a drug (or a different drug) has been used to refill the reservoir of IMD 12 than previously used, expiration of the initial delivery period may trigger a change from the previous flow rate of the prior drug concentration to the new flow rate of the drug concentration used to refill the reservoir.

The initial delivery period may be determined, based on the flow rate, concentration profile, and target transition dose of the drug to be delivered to patient 1, by one or more devices of system 10. The initial delivery period may be determined for a prime bolus or a bridge bolus (and the corresponding subsequent portion of the mixed fluid), depending upon the type of transition of drug delivery for patient 1. In some examples, IMD 12 may be the device configured to determine the initial delivery period. In other examples, external programmer 20 may be the device configured to determine the initial delivery period. However, other devices may determine the initial delivery period or a combination of two or more devices may be configured to determine the initial delivery period.

Once the initial delivery period has been determined, system 10 may perform the delivery transition. In the example of transitioning from drug delivery from one drug source (e.g., external drug pump 26) to another drug source (e.g., IMD 12), system 10 may be configured to track the duration during which the first fluid is delivered to patient 1 by IMD 12 and determine that the duration exceeds the initial delivery period. Responsive to determining that the duration exceeds the initial delivery period, system 10 may output, for display via a display device (e.g., a display device of programmer 20 or external drug pump 26), an instruction for a user to terminate delivery of the second fluid from external drug pump 26.

In the example of transitioning between drugs of different concentrations, system 10 may also control IMD 12 to adjust the flow rate of the drug in response to expiration of the initial delivery period. For example, system 10 may be configured to track a duration during which the first fluid (e.g., fluid with a first concentration) is delivered to patient 1 prior to a second fluid (e.g., fluid with a second concentration) and determine that the duration exceeds the initial delivery period. If IMD 12 is refilled with a lesser concentration of the drug than previously contained within the reservoir, system 10 may, responsive to determining that the duration exceeds the initial delivery period, control IMD 12 to increase the flow rate to a second flow rate. If IMD 12 is refilled with a greater concentration of the drug than previously contained within the reservoir, system 10 may, responsive to determining that the duration exceeds the initial delivery period, control IMD 12 to decrease the flow rate to a second flow rate. In this manner, system 10 may automatically control when the drug delivery flow rate is changed to account for mixing between the different drug concentrations within catheter 14.

System 10 may also include one or more display devices. For example, programmer 20, external drug pump 26, or another device may include a display device configured to present various information related to the initial delivery period, drug concentrations, target transition dose, target prescribed dose, and/or any other aspect of therapy. In one example, one or more of IMD 12, programmer 20 and/or external drug pump 26 may be configured to output, for presentation at the display device, a graph of a total output dose of the drug delivered to the patient with respect to time, a representation of the target transition dose with respect to the total output dose, and an indication of the initial delivery period. The total output dose may be the actual dose being delivered to patient 1 at any given time. The target transition dose may be a limit, marker, numeral, percentage, or any other representation of the target transition dose. System 10 may also be configured to output, for presentation at the display device, a first dosing portion representing dosing from drug delivered via the reservoir of IMD 12 when IMD 12 includes a drug pump coupled to the reservoir. System 10 may further be configured to output, for presentation at the display device, a second dosing portion representing dosing from drug delivered from external drug pump 26. The sum of the first dose portion and the second dose portion represents the total output dose.

FIG. 1 is described with respect to transition of drug delivery between external drug pump 26 and IMD 12, such as when external drug pump 26 is being removed after IMD 12 is implanted within patient 1. In other examples, two or more external drug pumps may be used to delivery drug prior to the transition to IMD 12 or external drug pump 26 may be transitioned to a different external drug pump. In each of these transitions, a prime bolus of a fluid may be delivered to patient 1 to initiate delivery with the new device prior to termination of drug delivered from the previous device. In other examples, the transition of drug delivery may be between two different concentrations of a drug or two different types of drugs that occurs when the reservoir of IMD 12 is refilled. This transition may be referred to as a bridge bolus in which the transition period, and the initial delivery period covers the period of time in which a mixture of each drug is delivered to patient 1 via catheter 14.

System 10 may be configured to delivery any one or more different types of drugs. For example, system 10 may be used to deliver morphine, baclofen, ziconotide, various proteins, or any other therapeutic agent directed for treatment of a patient condition. These therapeutic agents are only examples, and system 10 may not be limited to any type of drug deliverable for treatment of patient 1. Furthermore, one or more components of system 10 may be selected to be compatible with any therapeutic agent of fluid to be delivered to patient 1.

Although the target therapy delivery site described with reference to the foregoing examples is proximate to the spinal cord of a patient, other applications of therapy systems in accordance with this disclosure include alternative delivery sites. In some examples, the target delivery site may be proximate to different types of tissues including, e.g., nerves (e.g., sacral, pudendal or perineal nerves), organs, muscles or muscle groups. In one example, a catheter may be positioned to deliver a therapeutic fluid to a deep brain site or within the heart or blood vessels. For example, system 10 may be configured to deliver a therapeutic agent (e.g., treprostinil) to the heart of patient 1 in order to treat symptoms related to pulmonary arterial hypertension (PAH). In response to determining that the initial delivery period elapsed, programmer 20 or external drug pump 26 may present an instruction to the clinician to terminate delivery of fluid from external drug pump 26 and/or remove catheter 28 from patient 1. Some patients may be sensitive to small dosage changes of treprostinil. The concentration profile and target transition dose described herein may be used to minimize the risk of an overdose, and an underdose, of treprostinil to patient 1 when a drug transition must occur during therapy.

Delivery of a therapeutic fluid within the brain may help manage a number of disorders or diseases including, e.g., chronic pain, diabetes, depression or other mood disorders, dementia, obsessive-compulsive disorder, migraines, obesity, and movement disorders, such as Parkinson's disease, spasticity, and epilepsy. A catheter may also be positioned to deliver insulin to a patient with diabetes. In other examples, the system may deliver a therapeutic fluid to various sites within a patient to facilitate other therapies and to manage other conditions including peripheral neuropathy or post-operative pain mitigation, ilioinguinal nerve therapy, intercostal nerve therapy, gastric drug induced stimulation for the treatment of gastric motility disorders and/or obesity, and muscle stimulation, or for mitigation of peripheral and localized pain e.g., leg pain or back pain.

Figure 2:
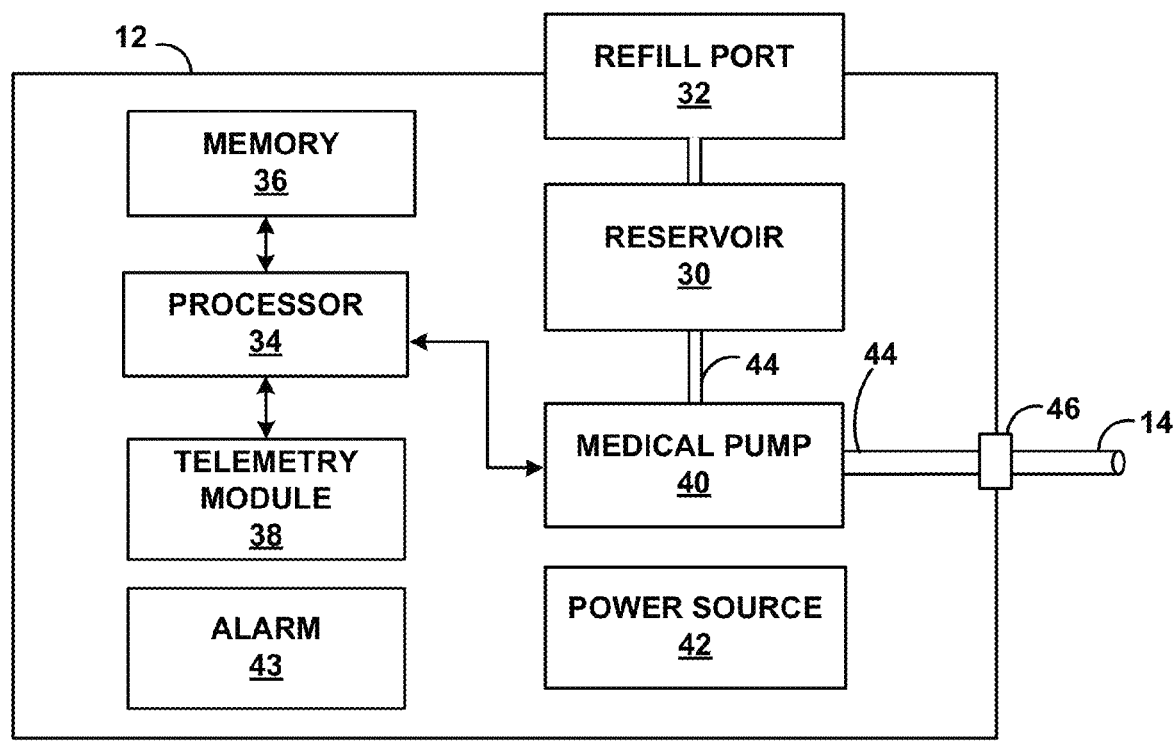
FIG. 2 is functional block diagram of the example IMD of FIG. 1.

FIG. 2 is functional block diagram illustrating components of example IMD 12 of FIG. 1. The example IMD 12 shown in FIG. 2 includes reservoir 30, refill port 32, processor 34, memory 36, telemetry module 38, medical pump 40, power source 42, alarm 43, internal channels 44, and catheter access port (CAP) 46. IMD 12 is also shown coupled to catheter 14. IMD 12 may also include sensors that are used to determine the status of medical pump 40 or other components within IMD 12, such as a pressure sensor used to measure the pressure at the outlet of medical pump 40.

Refill port 32 provides for refilling of reservoir 30 with therapeutic fluid (e.g., a drug in liquid form). Refill port 32 may comprise a self-sealing injection port. The self-sealing injection port may include a self-sealing membrane to prevent loss of therapeutic agent delivered to reservoir 30 via refill port 32. After a delivery system, e.g., a hypodermic needle, penetrates the membrane of refill port 32, the membrane may seal shut when the delivery system is removed from refill port 32. Internal channels 44 may comprise one or more segments of tubing and/or a series of cavities that run from reservoir 30, around or through medical pump 40 to catheter access port 46.

Processor 34 may include one or more processors and be configured to control the operation of medical pump 40 with the aid of software instructions associated with program information that is stored in memory 36. In one example, processor 34 is configured to run the software instructions in order to control operation of IMD 12. For example, the software instructions may define one or more therapy programs that specify the amount of a therapeutic agent (e.g., drug) that is delivered to a target tissue site within patient 1 from reservoir 30 via catheter 14, e.g., dose, the rate at which the agent is delivered, e.g., dosage rate, flow rate, and the time at which the agent will be delivered and the time interval over which the agent will be delivered, e.g., the therapy schedule for dose or doses defined by program. In other examples, a quantity of the therapeutic agent may be delivered, at least in part, according to one or more physiological characteristics of a patient, e.g., physiological characteristics sensed by one or more sensors (not shown) implanted within a patient as part of therapy system 10 (FIG. 1), or according to a combination of scheduled doses and physiological characteristics. In some examples, a patient may be permitted to increase or reduce one or more doses. In addition, memory 36 may include instructions regarding the determination of an initial delivery period for a transition in drug delivery as described herein.

Processor 34, as well as other processors described herein, can include one or more processors, including one or more microprocessors, digital signal processors (DSPs), application specific integrated circuits (ASICs), field programmable gate arrays (FPGAs), or any other equivalent integrated or discrete logic circuitry, as well as any suitable combination of such components. The term "processor" or "processing circuitry" may generally refer to any of the foregoing logic circuitry, alone or in combination with other logic circuitry, or any other equivalent circuitry. The functions attributed to processors described herein may be provided by a hardware device and embodied as software, firmware, hardware, or any combination thereof.

Memory 36 may include any volatile or non-volatile media, such as a random access memory (RAM), read only memory (ROM), non-volatile RAM (NVRAM), electrically erasable programmable ROM (EEPROM), flash memory, and the like. As mentioned above, memory 36 may store program information including instructions for execution by processor 34, such as, but not limited to, therapy programs, historical therapy programs, timing programs for delivery of the therapeutic agent from reservoir 30 to catheter 14, instructions for transitioning drug delivery (e.g., delivering a prime bolus or a bridge bolus) and any other information regarding therapy of patient 1. Memory 36 may include separate memory portions for storing instructions, patient information, therapy parameters (e.g., grouped into sets referred to as "dosing programs"), therapy adjustment information, program histories, and other categories of information such as any other data that may benefit from separate physical memory modules.

Telemetry module 38 in IMD 12, as well as telemetry modules in programmers, such as external programmer 20, may accomplish communication by any suitable technique, such as RF communication techniques. In addition, telemetry module 38 may communicate with programmer 20 via proximal inductive interaction of IMD 12 with external programmer 20. Processor 34 controls telemetry module 38 to send and receive information. In other examples, telemetry module 38 may also exchange data with external drug pump 26 of FIG. 1 or other devices.

Power source 42 delivers operating power to various components of IMD 12. Power source 42 may include a small rechargeable or non-rechargeable battery and a power generation circuit to produce the operating power. In the case of a rechargeable battery, recharging may be accomplished through proximal inductive interaction between an external charger and an inductive charging coil within IMD 12. In some examples, power requirements may be small enough to allow IMD 12 to utilize patient motion and implement a kinetic energy-scavenging device to trickle charge a rechargeable battery. In other examples, non-rechargeable storage devices may be used for a limited period of time. As a further alternative, an external inductive power supply could transcutaneously power IMD 12 whenever measurements are needed or desired.

Medical pump 40 may be a mechanism that is configured to deliver a drug in some metered or other desired flow rate or dosage to target site 2 within patient 1 from reservoir 30 via catheter 14. For example, medical pump 40 may include an actuation mechanism that is electrically energized to provide a pump stroke to move fluid from reservoir 30. The actuation mechanism may comprise an electromagnetic coil and an actuator that is movable in response to electrical energization of the coil. Other actuation mechanisms may be used, such as a piezoactuator. Medical pump 40 may be configured to deliver drug with a variety of different programmable flow rates.

Alarm 43 may include one or more components configured to convey information to patient 1 regarding therapy delivery. As examples, alarm 43 may include a speaker to provide audible signals, a vibration device configured to provide haptic feedback, and/or one or more electrodes to provide an electrical stimulus. Processor 34 may be configured to operate alarm 43 to signal an empty or near-empty reservoir 30, a malfunction of IMD 12, or when the initial delivery period has expired. Alarm 43 may thus inform patient 1 that a change in drug delivery will occur (e.g., a change in therapy program, initializing a transition period with a new drug or different drug concentration, or change in flow rate). In some examples, alarm 43 may prompt patient 1 and/or the clinician to turn off delivery of drug from external drug pump 26 in response to expiration of the initial delivery period.

Figure 3:
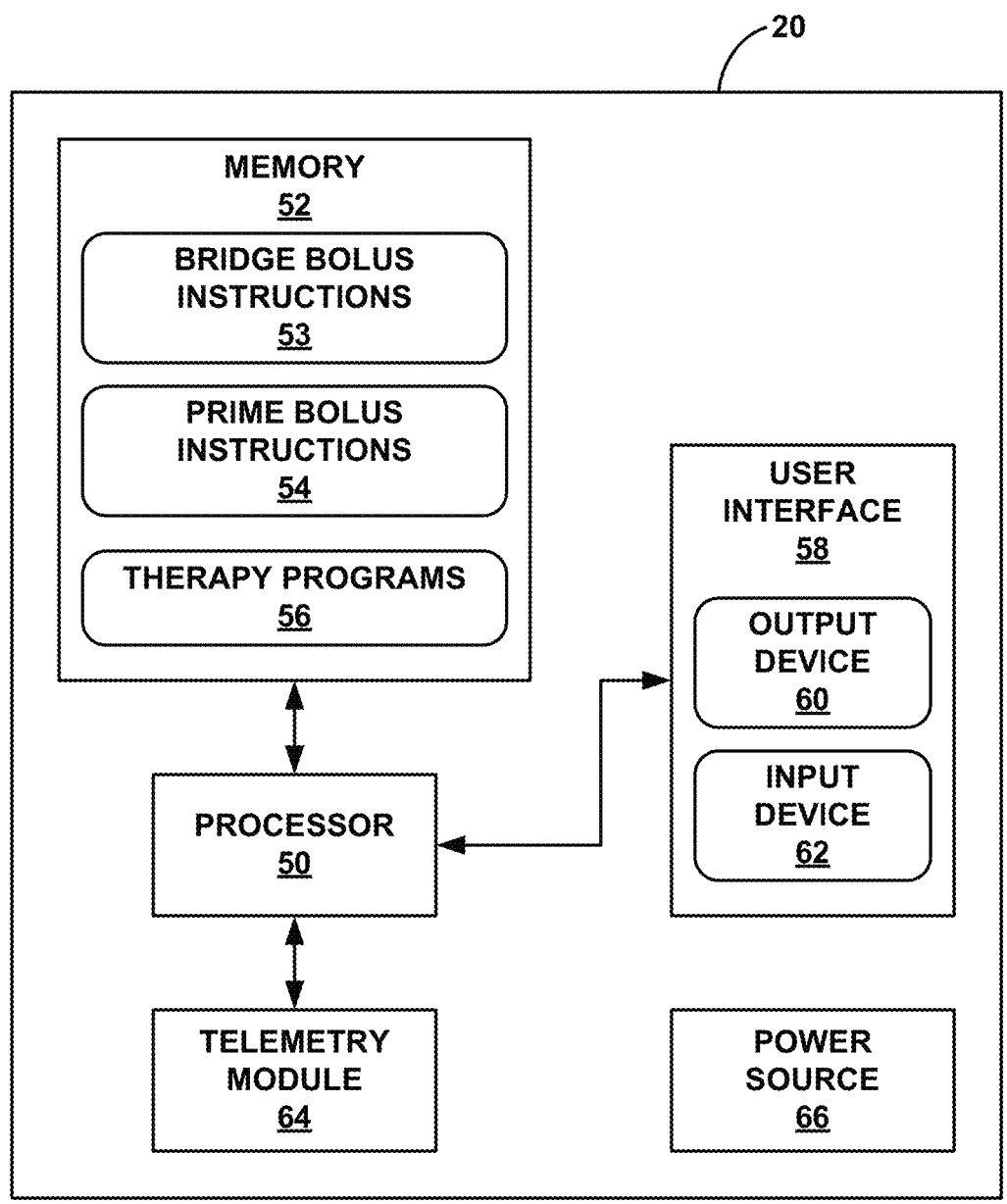
FIG. 3 is a functional block diagram of the example external programmer of FIG. 1.

FIG. 3 is a functional block diagram of example external programmer 20 of FIG. 1. Although programmer 20 may generally be described as a hand-held device, in other examples, programmer 20 may be a larger portable device or a more stationary device. In addition, in other examples, programmer 20 may be included as part of an external charging device or include the functionality of an external charging device. As illustrated in FIG. 3, programmer 20 may include a processor 50, memory 52, user interface 58, telemetry module 64, and power source 66. Memory 52 may store instructions that, when executed by processor 50, cause processor 50 and external programmer 20 to provide the functionality ascribed to external programmer 20 throughout this disclosure.

In general, programmer 20 comprises any suitable arrangement of hardware, alone or in combination with software and/or firmware, to perform the techniques attributed to programmer 20, and processor 50, user interface 58, and telemetry module 64 of programmer 20. In various examples, programmer 20 may include one or more processors, such as one or more microprocessors, DSPs, ASICs, FPGAs, or any other equivalent integrated or discrete logic circuitry, as well as any combinations of such components. Programmer 20 also, in various examples, may include a memory 52, such as RAM, ROM, PROM, EPROM, EEPROM, flash memory, a hard disk, a CD-ROM, comprising executable instructions for causing the one or more processors to perform the actions attributed to them. Moreover, although processor 50 and telemetry module 64 are described as separate modules, in some examples, processor 50 and telemetry module 64 are functionally integrated. In some examples, processor 50 and telemetry module 64 correspond to individual hardware units, such as ASICs, DSPs, FPGAs, or other hardware units.

Memory 52 (e.g., a storage device) may store instructions that, when executed by processor 50, cause processor 50 and programmer 20 to provide the functionality ascribed to programmer 20 throughout this disclosure. For example memory 52 may include instructions that cause processor 50 to obtain a therapy programs from memory, generate therapy programs, receive a user input and send a corresponding commands to IMD 12, determine initial delivery periods, or any other functionality. In addition, memory 52 may include a plurality of therapy programs, where each program includes a parameter set (e.g., delivery times and flow rates) that defines therapy.

In the example shown in FIG. 3, memory 52 stores, among other data, bridge bolus instructions 53, prime bolus instructions 54, and therapy programs 56 in separate memories within memory 52 or separate areas within memory 52. Each stored therapy program 56 defines a particular set of drug delivery parameters that may define therapy delivery from IMD 12 and/or external drug pump 26. These parameters may include drug concentrations, flow rates, times or schedules for fluid delivery, error conditions and error handing, or any other information related to delivery of therapy to patient 1. Therapy programs 56 may be predefined and stored in memory 52, adjusted by a user, and/or generated from user input. One or more of therapy programs 56 may be transmitted to IMD 12 and/or external drug pump 26 via wired or wireless communication.

Memory 52 may also include bridge bolus instructions 53. Bridge bolus instructions 53 may include instructions related to determining one or more parameters of a bridge bolus of drug to be delivered to patient 1 during a transition period between different drugs or different concentrations of drugs. Bridge bolus instructions 53 may include concentration profiles for one or more drugs, flow rate information for various dosages, one or more proposed target transition doses, and/or instructions for determining the initial delivery period when transitioning to a different drug or different drug concentration. These instructions for determining the initial delivery period may include one or more look-up tables, formulas, or algorithms, such as those described with respect to FIGS. 7, 10A, 10B, and 11. In some examples, bridge bolus instructions 53 may also store predetermined initial delivery periods and/or initial delivery periods generated by system 10 such as programmer 20 or IMD 12.

Memory 52 may also include prime bolus instructions 54. Prime bolus instructions 54 may include instructions related to determining one or more parameters of a prime bolus of drug to be delivered to patient 1 and subsequent portion of mixed fluid during a transition period in which a drug is initially delivered to patient 1 from a newly implanted IMD 12 and/or catheter 14. This prime bolus may be delivered when transitioning from delivery via another device (e.g., external drug pump 26) to deliver via IMD 12. Prime bolus instructions 54 may include concentration profiles for one or more drugs, flow rate information for various dosages, one or more proposed target transition doses, and/or instructions for determining the initial delivery period when initially delivering drug from reservoir 30 of IMD 12, for example, and the inert fluid within catheter 14. These instructions for determining the initial delivery period may include one or more look-up tables, formulas, or algorithms, such as those described with respect to FIGS. 7, 9, and 10, for example. In some examples, prime bolus instructions 54 may also store predetermined initial delivery periods and/or initial delivery periods generated by system 10 such as programmer 20 or IMD 12.

User interface 58 may include one or more output device 60 (e.g., a display device) and one or more input device 62. Output device 60 may include, lights, a speaker for voice commands, a display device, such as a liquid crystal (LCD), light-emitting diode (LED), or organic light-emitting diode (OLED). Input device 62 may include one or more of a button, keypad, pointing device, or presence-sensitive display. In some examples the display device may be a touch screen (e.g., a presence-sensitive screen). User interface 58 may be configured to display any information related to the delivery of therapy, concentration profiles, target transition doses, target prescription doses, initial delivery periods, or any other such information described herein. For example, user interface 58 may be configured to include user interface 230 of FIG. 12. User interface 58 may also receive user input via input device 62. The input may be, for example, in the form of pressing a button on a keypad or selecting an icon from a touch screen. The input may select a target transition dose, one or more drugs, one or more therapy programs, turn drug delivery on or off, or any other inputs related to drug delivery described herein.

Telemetry module 64 may support wireless communication between IMD 12 and programmer 20 under the control of processor 50. Telemetry module 64 may also be configured to communicate with another computing device (e.g., external drug pump 26) via wireless communication techniques, or direct communication through a wired connection. In some examples, telemetry module 64 may be substantially similar to telemetry module 38 (FIG. 2) of IMD 12 described herein, providing wireless communication via an RF or proximal inductive medium. In some examples, telemetry module 64 may include an antenna, which may take on a variety of forms, such as an internal or external antenna. Examples of local wireless communication techniques that may be employed to facilitate communication between programmer 20 and IMD 12 include RF communication according to the 802.11 or Bluetooth specification sets or other standard or proprietary telemetry protocols.

Figure 4:
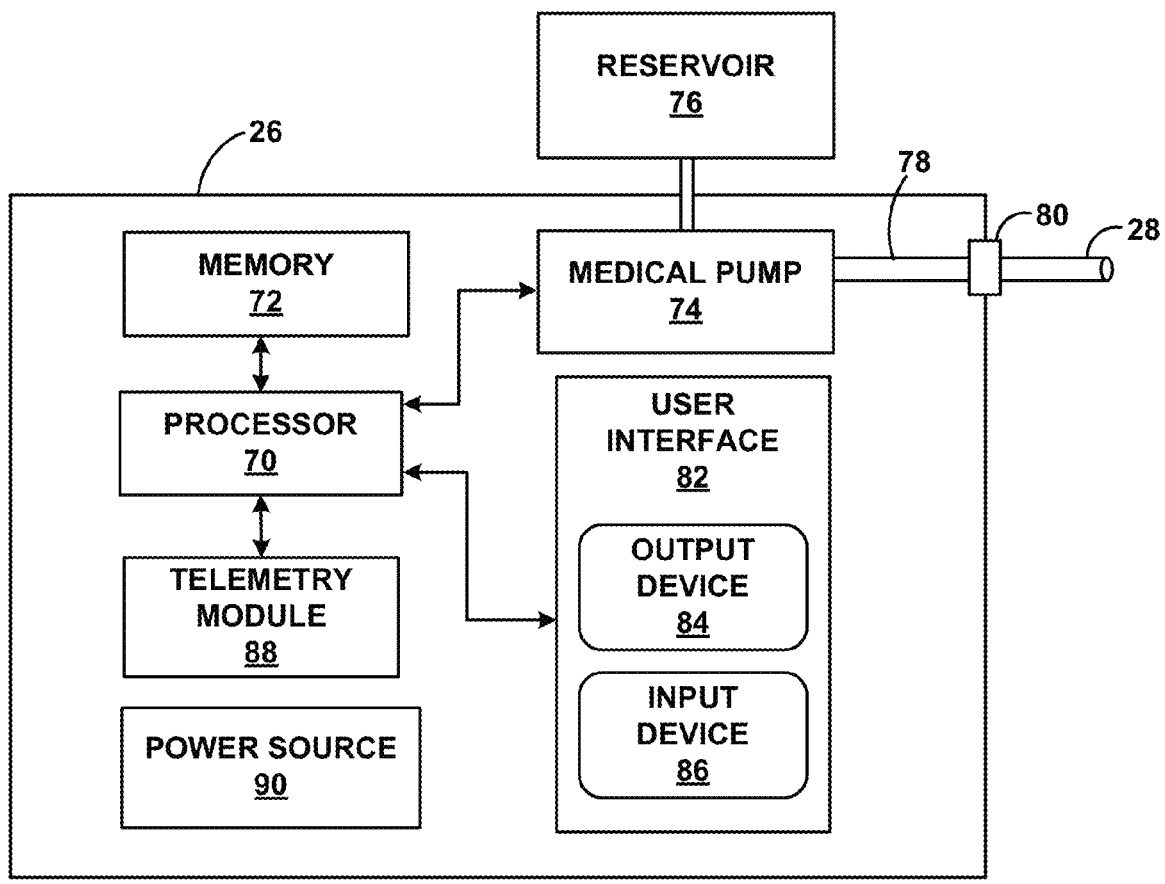
FIG. 4 is a functional block diagram of the example external drug pump of FIG. 1.

FIG. 4 is a functional block diagram of the example external drug pump 26 of FIG. 1. The example external drug pump 26 shown in FIG. 4 includes reservoir 76, processor 70, memory 72, telemetry module 88, medical pump 74, power source 90, internal channels 78, and catheter coupling 80. Medical pump 74 is also shown coupled to catheter 28. Reservoir 76 is shown as external to a housing of external drug pump 26, but reservoir 76 may be contained within the housing of external drug pump 26 in other examples. Reservoir 76 may be in the form of a gravity fed fluid bag or any other container configured to hold a fluid that will be delivered to patient 1. Internal channels 78 may comprise one or more segments of tubing and/or a series of cavities that run from reservoir 76, around or through medical pump 74 to catheter coupling 80.

Processor 70 may include one or more processors and be configured to control the operation of medical pump 74 with the aid of software instructions associated with program information that is stored in memory 72. In one example, processor 70 is configured to run the software instructions in order to control operation of external drug pump 26. For example, the software instructions may define one or more therapy programs that specify the amount of a therapeutic agent (e.g., drug) that is delivered to a target tissue site within patient 1 from reservoir 76 via catheter 28, e.g., dose, the rate at which the agent is delivered, e.g., dosage rate, flow rate, and the time at which the agent will be delivered and the time interval over which the agent will be delivered, e.g., the therapy schedule for dose or doses defined by program. In other examples, a quantity of the therapeutic agent may be delivered, at least in part, according to one or more physiological characteristics of a patient, e.g., physiological characteristics sensed by one or more sensors (not shown) implanted within a patient as part of therapy system 10 (FIG. 1), or according to a combination of scheduled doses and physiological characteristics. In some examples, a patient may be permitted to increase or reduce one or more doses. In addition, memory 72 may include instructions regarding the determination of an initial delivery period for a transition in drug delivery as described herein.

Processor 70 can include one or more processors, including one or more microprocessors, DSPs, ASICs, FPGAs, or any other equivalent integrated or discrete logic circuitry, as well as any suitable combination of such components. The term "processor" or "processing circuitry" may generally refer to any of the foregoing logic circuitry, alone or in combination with other logic circuitry, or any other equivalent circuitry.

Memory 72 may include any volatile or non-volatile media, such as a RAM, ROM, NVRAM, EEPROM, flash memory, and the like. As mentioned above, memory 72 may store program information including instructions for execution by processor 70, such as, but not limited to, therapy programs, historical therapy programs, timing programs for delivery of the therapeutic agent from reservoir 76 to catheter 28, instructions for transitioning drug delivery (e.g., delivering a prime bolus or bridge bolus and respective portions of mixed fluid during the initial delivery period) and any other information regarding therapy of patient 1. Memory 72 may include separate memory portions for storing instructions, patient information, therapy parameters (e.g., grouped into sets referred to as "dosing programs"), therapy adjustment information, program histories, and other categories of information such as any other data that may benefit from separate physical memory modules. For example, memory 72 may be similar to memory 52 of IMD 12 and include therapy programs, bridge bolus instructions, and/or prime bolus instructions.

Telemetry module 88 in external drug pump 26, as well as telemetry modules in programmers, such as external programmer 20, may accomplish communication by RF communication techniques. In addition, telemetry module 88 may communicate with IMD 12 via proximal inductive interaction of external drug pump 26 with external programmer 20. Processor 70 controls telemetry module 88 to send and receive information. In other examples, telemetry module 88 may also exchange data with external drug pump 26 of FIG. 1 or other devices.

Power source 90 delivers operating power to various components of external drug pump 26. Power source 90 may include a small rechargeable or non-rechargeable battery and a power generation circuit to produce the operating power. Alternatively, power source 90 may be a power converter configured to receive power from an external outlet or power supply.

Medical pump 74 may be a mechanism that is configured to deliver a drug in some metered or other desired flow rate or dosage to target site 2 within patient 1 from reservoir 76 via catheter 28. For example, medical pump 74 may include an actuation mechanism that is electrically energized to provide a pump stroke to move fluid from reservoir 76. The actuation mechanism may comprise an electromagnetic coil and an actuator that is movable in response to electrical energization of the coil. Other actuation mechanisms may be used, such as a piezoactuator. Medical pump 74 may be configured to deliver drug with a variety of different programmable flow rates. Medical pump 74 may be similar to medical pump 40 (FIG. 2) of IMD 12.

External drug pump 26 may also include user interface 82. User interface 82 may include one or more output device 84 (e.g., a display device) and one or more input device 86. Output device 84 may include, lights, a speaker for voice commands, a display device, such as a LCD, LED, or OLED. Input device 86 may include one or more of a button, keypad, pointing device, or presence-sensitive display. In some examples the display device may be a touch screen (e.g., a presence-sensitive screen). User interface 82 may be configured to display any information related to the delivery of therapy, concentration profiles, target transition doses, target prescription doses, initial delivery periods, or any other such information described herein. For example, user interface 82 may be configured to include user interface 230 of FIG. 12. User interface 82 may also receive user input via input device 86. The input may be, for example, in the form of pressing a button on a keypad or selecting an icon from a touch screen. The input may select a target transition dose, one or more drugs, one or more therapy programs, turn drug delivery on or off, or any other inputs related to drug delivery described herein. In some examples, user interface 82 may, in response to the initial delivery period elapsing, instruct a user to terminate delivery of drug from external drug pump 26.

Figure 5:
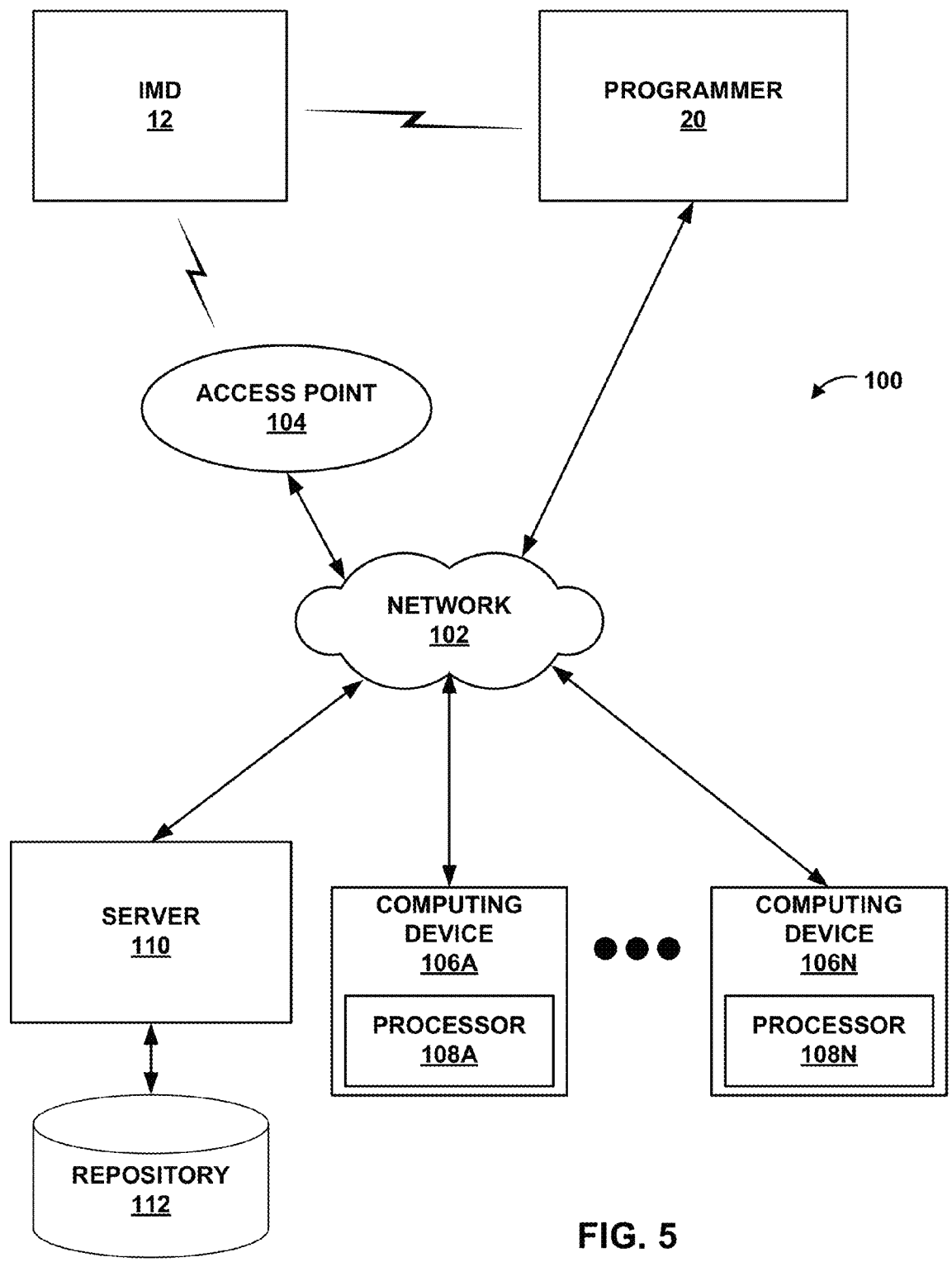
FIG. 5 is a block diagram illustrating an example system that includes a networked server coupled to an IMD and one or more computing devices via a network.

FIG. 5 is a block diagram illustrating an example system 100 that includes a networked server 110 coupled to IMD 12 and one or more computing devices 106 via network 102. As shown in FIG. 5, server 110 (e.g., a networked external computing device) and one or more computing devices 106A-106N (collectively "computing devices 106") that are coupled to the IMD 12 and programmer 20 shown in FIG. 1 via a network 102. In some examples, network 102 can be used to transmit therapy programs, concentration profiles, target transition doses, initial delivery periods, sensed patient data, or any other information between IMD 12, programmer 20, external drug pump 26, server 110 and/or computing devices 106.

Figure 7:
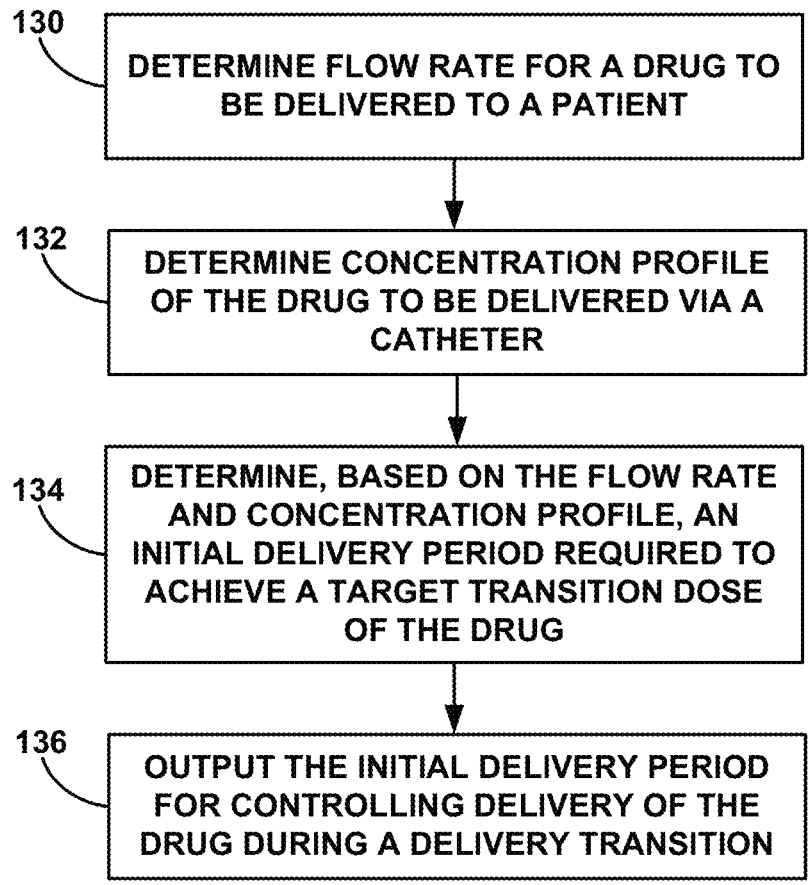
FIG. 7 is a flow diagram of an example technique for determining an initial delivery period needed to achieve a target transition dose of a drug.

In some examples, IMD 12 and/or programmer 20 may transmit flow rates, concentration profiles, and/or target transition doses to server 110 and/or computing devices 106 for processing and determination of an initial delivery period, e.g., using the technique described with respect to FIG. 7. Calculating the initial delivery period may computationally intensive and require additional power in some examples. In addition, in some examples, server 110 and/or computing devices 106 may generate the concentration profile based on experimental data or other data points. Offloading tasks like these to server 110, for example, may provide for faster determination (e.g., calculation) of parameters and prevent excess drain of battery power from programmer 20 and/or IMD 12. Once server 110 determines the initial delivery period, for example, server 110 may transmit the set of values back to programmer 20 and/or IMD 12.

In other examples, the information transmitted by IMD 12 may allow a clinician or other healthcare professional to monitor patient 1 remotely. In some examples, IMD 12 may use telemetry module 38 (FIG. 2) to communicate with programmer 20 via a first wireless connection, and to communicate with access point 104 via a second wireless connection, e.g., at different times. In the example of FIG. 5, access point 104, programmer 20, server 110 and computing devices 106 are interconnected, and able to communicate with each other through network 102. In some cases, one or more of access point 104, programmer 20, server 110 and computing devices 106 may be coupled to network 102 via one or more wireless connections. IMD 12, programmer 20, server 110, and computing devices 106 may each comprise one or more processors, (e.g., processors 108A and 108N, respectively), such as one or more microprocessors, DSPs, ASICs, FPGAs, programmable logic circuitry, or the like, that may perform various functions and operations, such as those described herein.

Access point 104 may comprise a device that connects to network 102 via any of a variety of connections, such as telephone dial-up, digital subscriber line (DSL), or cable modem connections. In other examples, access point 104 may be coupled to network 102 through different forms of connections, including wired or wireless connections. In some examples, access point 104 may be co-located with patient 1 and may comprise one or more programming units and/or computing devices (e.g., one or more monitoring units) that may perform various functions and operations described herein. For example, access point 104 may include a home-monitoring unit that is co-located with patient 1 and that may monitor the activity of IMD 12. In some examples, server 110 or computing devices 106 may control or perform any of the various functions or operations described herein.

In some cases, server 110 may be configured to provide a secure storage site (e.g., via repository 112) for therapy parameters, concentration profiles, target prescribed doses, target transition doses, initial delivery periods, sensed data, or other data that has been collected and generated from IMD 12 and/or programmer 20. Network 102 may comprise a local area network, wide area network, or global network, such as the Internet. The system of FIG. 5 may be implemented, in some aspects, with general network technology and functionality similar to that provide by the Medtronic CareLink® Network developed by Medtronic, Inc., of Minneapolis, Minn.

Figure 6:
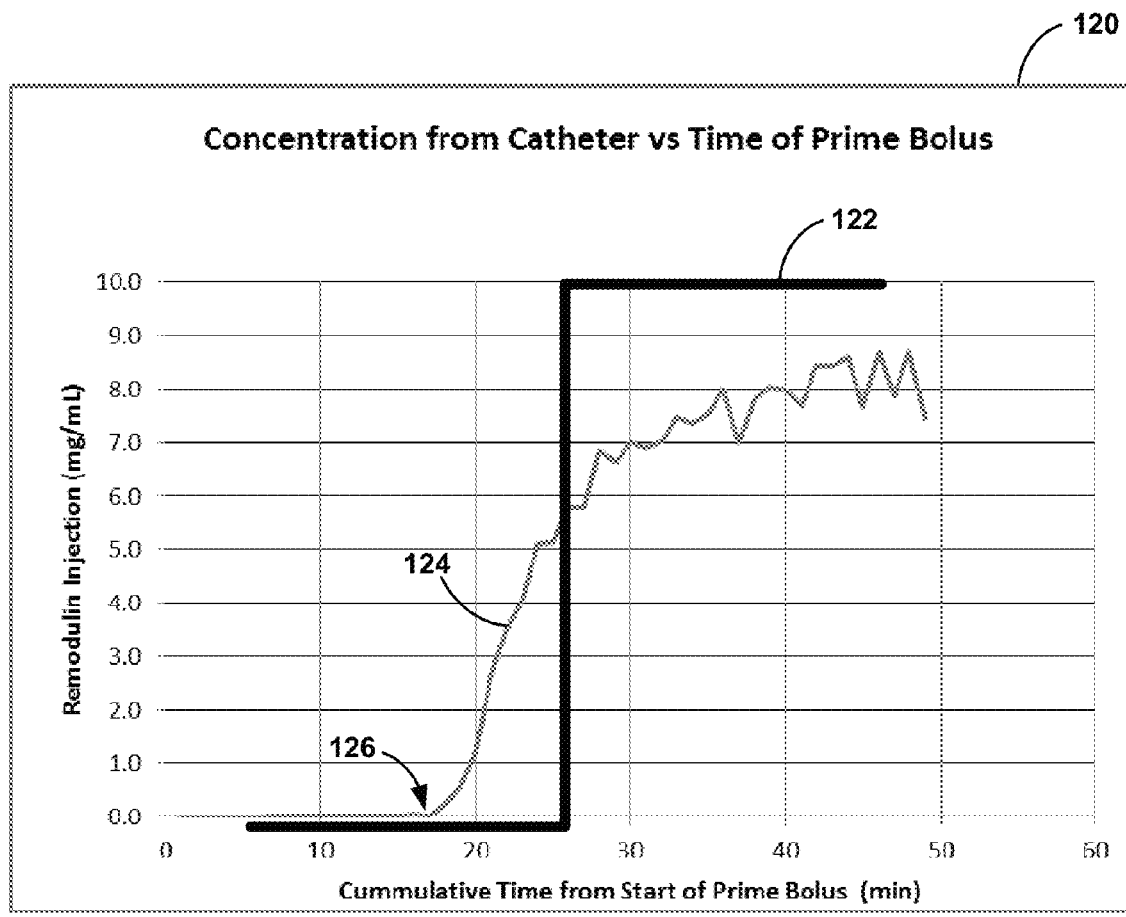
FIG. 6 is a graph illustrating an example concentration of a drug when delivered over time.

FIG. 6 is a graph illustrating an example concentration profile of a drug when delivered over time. As shown in FIG. 6, graph 120 represents an example of how a drug may be delivered to patient 1 during and after a prime bolus. Graph 120 will be described with respect to IMD 12 and catheter 14, but any other drug delivery system may be subject to a similar scenario. Upon implantation of IMD 12 and catheter 14 in patient 1, a drug may be contained or injected into reservoir 30 of IMD 12. Catheter 14, and one or more fluid passages of IMD 12, may include an inert liquid to prevent air from being delivered to patient 1. The inert liquid may be water, saline, or some other physiologically compatible fluid to occupy the passages of IMD 12 and catheter 14. The example of FIG. 6 is described with regard to the drug Remodulin™ (i.e., treprostinil) available from United Therapeutics Corporation, but the concept of a concentration profile may be applicable to any other drug or therapeutic agent.

The interface between the drug (e.g., treprostinil) and the inert fluid may not be highly defined. Line 122 indicates an idealized delivery of drug without any mixing of the drug and the fluid prior to the drug reaching patient tissue. According to line 122, the drug dosage may remain at zero until all of the inert fluid is expelled from catheter 14 so that the full concentration of the drug immediately reaches patient 1 at once. This spike in concentration is shown at approximately the 26 minute mark where the concentration of treprostinil immediately changes from zero to 10 milligrams per milliliter (mg/ml). However, this concentration profile may not reflect the actual mixing that occurs at the interface between the drug and the inert fluid.

Instead of remaining segregated, the drug may mix with the inert fluid as both the dug and fluid are forced out of IMD 12 and catheter 14. As shown in line 124, the output concentration of the drug may remain at zero until some drug that has mixed with the fluid begins to reach the end of catheter 14 (e.g., the end of the prime bolus). At time point 126, the first portion of drug that has mixed with the fluid (i.e., the mixed fluid) begins to exit catheter 14. As fluid is continued to be pumped out of IMD 12 and catheter 14, the concentration of drug being delivered to patient 1 increases. In other words, over time, as the full concentration of the drug moves from reservoir 30, a greater and greater concentration of the drug exits catheter 14 and is delivered to patient 1. This increase in concentration shown in line 124 continues until all of the inert fluid has exited IMD 12 and catheter 14 and the fluid exiting catheter 14 is substantially the full concentration of the drug contained within reservoir 30.

Line 124 may represent the concentration profile of the drug treprostinil in some examples in which treprostinil having a concentration of 10 mg/ml is stored in reservoir 30 (FIG. 2) of IMD 12. In other words, the rate of concentration change and curve of line 124 may be indicative of the mixing or diffusion that occurs between the drug and fluid within IMD 12 and catheter 14. Using the concentration profile of line 124, system 10 (e.g., a processor of one or more IMD 12, programmer 20, external drug delivery device 26, or another device) may determine an initial delivery period of the drug from IMD 12 required to achieve the target transition dose with the portion of mixed fluid after the prime bolus (e.g., the volume of fluid that include an inert fluid prior to the therapeutic agent stored within the reservoir). For example, if the target transition dose is 120 percent of the target prescribed dose (e.g., 10.0 mg/ml) when also delivering the drug via external drug pump 26, system 10 may determine that the initial delivery period is 21 minutes when line 124 indicates that approximately 2.0 mg/ml (i.e., 20 percent of 10 mg/ml) concentration of the drug is being delivered to patient 1 from IMD 12.

The characteristics (e.g., slope) of line 124 indicating the concentration profile of treprostinil may be dependent on several factors. For example, the concentration profile may be dependent upon the flow rate of the fluid out of catheter 14, the length of catheter 14, the cross-sectional area of catheter 14, viscosities of the fluids, and the temperature of the fluid and drug. The concentration profile may also be dependent upon how the different fluids are added to the fluid path and where the interface is located within the fluid path. For example, interface locations may be where catheter port 48 meets catheter 14 or where reservoir 30 meets internal passage 44. Upstream locations may allow greater time for mixing and different diameters in the fluid path may affect how large of an area the two fluids contact each other. For a single drug or drug combination, different concentration profiles may be determined for several values of each of these factors (e.g., different flow rates and catheter lengths) for typical uses within patients and/or extrapolation to any type or size of IMD 12 and catheter 14 implanted within patient 1. These different concentration profiles may be stored by memory 36 of IMD 12, memory 52 of programmer 20, memory 72 of external drug pump 26, or a memory of another device.

Graph 120 indicates the concentration profile for mixing between the full concentration of the drug and an inert fluid without any drug. However, similar concentration profiles may be determined for mixing between two fluids with different concentrations of the same or different drug. Such a scenario may occur when changing drug concentrations in reservoir 30 of IMD 12. Delivering drug over this transition may be called delivery of a bridge bolus. The concentration profile may change from the first concentration to the second concentration over time based on the factors indicated above.

FIG. 7 is a flow diagram of an example process for determining an initial delivery period needed to achieve a target transition dose of a drug. Although FIG. 7 will be described with respect to processor 34 of IMD 12, similar processes can be performed by one or more processor 50 and programmer 20, processor 80 and external drug pump 26, server 110, or another device, alone or in combination with each other or processor 34. Other sets of devices may also be used in other examples. The technique of FIG. 7 may be applicable to any drug delivery transitions, such as transitions between two different drug sources and/or transitions between two different drug concentrations of the same drug.

As shown in FIG. 7, processor 34 determines the flow rate for the drug to be delivered to patient 1 (130). This flow rate may be the flow rate of the new drug to be delivered or the flow rate of the current concentration of the drug, and the flow rate may be specified by a drug delivery schedule and/or calculated based on a target prescribed dose of the therapeutic agent. Processor 34 may determine the flow rate by, for example, obtaining a flow rate stored by memory 52. Processor 34 may also determine the concentration profile of the drug to be delivered via catheter 14 (132). In some examples, the concentration profile may be predetermined (e.g., experimentally determined or modeled based on known factors) and stored by memory 52, such as a part of bridge bolus instructions 53 or prime bolus instructions 54. In addition to, or instead of, predetermined concentration profiles, in some examples, processor 34 may extrapolate or calculate the concentration profile based on known data points to fie the therapy parameters of patient 1. However, processor 34 may request the flow rate and/or the concentration profile from another device, such as programmer 20 in other examples.

Processor 34 may then determine, based on the obtained flow rate and concentration profile, an initial delivery period required to achieve the target transition dose of the drug (134). The target transition dose may be predetermined based on the type of drug and/or patient condition or selected by received user input. Processor 34 may determine the initial delivery period by at least calculating the amount of time (i.e., the initial delivery period) that the prime bolus or the bridge bolus, and the corresponding portion of the mixed fluid, may be delivered to patient 1 until the target transition dose is reached at patient 1.

Processor 34 may then output the initial delivery period for controlling delivery of the drug during the delivery transition of the drug (136). In some examples, processor 34 presents the output to the user via a user interface (e.g., of programmer 20) as an instruction for manually terminating delivery of the drug via another drug source. In addition to, or instead of, the instruction, the output may be in the form of a command that processor 34 transmits to automatically turn off drug delivery by at least one of IMD 12 and external drug delivery device 26, adjust a flow rate of the drug delivery by at least one of IMD 12 and external drug delivery device 26, and/or turn on drug delivery by at least one of IMD 12 and external drug delivery device 26. Examples of this process, in the form of prime bolus delivery and bridge bolus delivery, and the subsequent delivery of mixed fluid, are described with respect to FIGS. 8-11.

Figure 8:
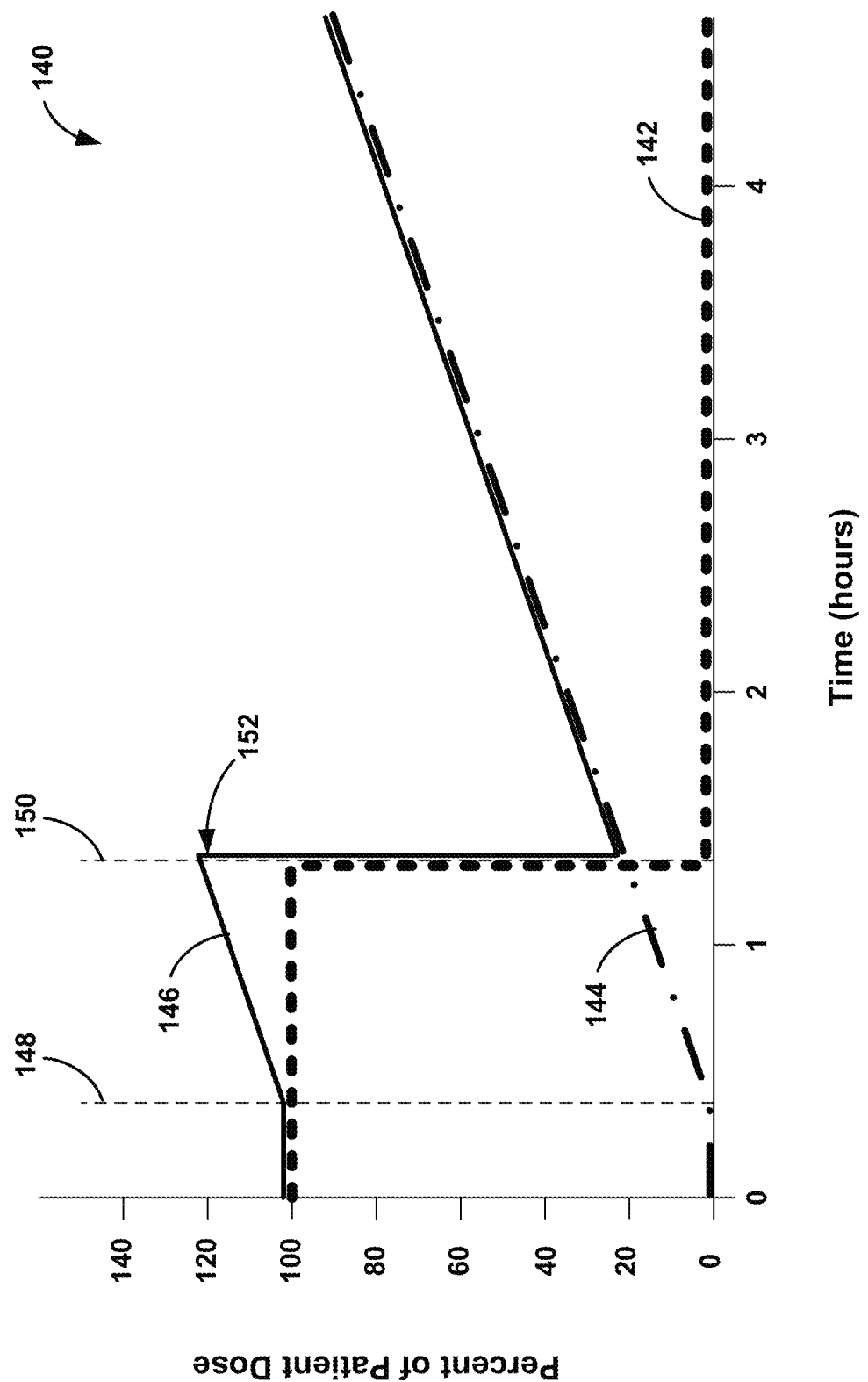
FIG. 8 is a graph illustrating an example total drug dosage delivered to a patient during the transition from an external drug pump to an IMD.

FIG. 8 is a graph illustrating an example total drug dosage delivered to patient 1 during the transition from drug delivery via external drug pump 26 to drug delivery via IMD 12. As shown by graph 140 of FIG. 8, patient 1 may receive a drug from two different sources simultaneously to achieve target transition dose 152 during a transition period. Dosage 142 represents the dosage of drug delivered by external drug pump 26 as indicated by the dosage of 100 percent when no time has yet elapsed. Dosage 144 represents the dosage of drug delivered by IMD 12 after delivery of the prime bolus is complete at time marker 148. A portion of the mixed fluid from IMD 12 is this delivered between time markers 148 and 150. Total output dose 146 represents the summed total dosage of the drug from both of IMD 12 and external drug pump 26.

Initially, both external drug pump 26 and IMD 12 deliver fluid to patient 1. However, IMD 12 does not initially contribute any drug to total output dose 146. The first portion of dosage 144 from time zero to time marker 148 only includes inert fluid from catheter 14 and IMD 12. At time marker 148 (e.g., at approximately 18 minutes), drug from reservoir 30 first reaches the exit of catheter 14 as partially mixed with the fluid of catheter 14. Therefore, between time marker 148 and time marker 150, dosage 144 increases as the concentration of the drug increases in the fluid exiting catheter 14. The volume of fluid delivered from time zero to time marker 148 may be referred to as the prime bolus, and the volume of fluid delivered from time marker 148 to time marker 150 may be referred to as a portion of the mixed fluid. Since patient 1 receives fluid from both IMD 12 and external drug pump 26, total output dose 146 reflects the sum of both dosage 144 and dosage 146. In other words, each of dosages 142 and 144 are respective portions of the total dosage of the drug delivered to patient 1.

At time marker 150, total output dose 146 reaches target transition dose 152. Target transition dose 152 is shown at approximately 120 percent of the target prescribed dosage. The target transition dose 152 may be selected as a maximum dose received by the patient during the transition from external drug pump 26 to IMD 12. The initial delivery period may be defined by the time period from time zero to time marker 150. At the expiration of the initial delivery period, programmer 20 may cause the termination of drug delivery (e.g., via a direct command or prompt presented to a user) from external drug pump 26 such that dosage 142 is reduced to zero. For example, external drug pump 26 may automatically terminate drug delivery or programmer 20 or another device may present instructions to the user to terminate delivery via external drug pump 26.

After external drug pump 26 terminates delivering drug to patient 1, dosage 142 remains at zero percent of the patient dose and dosage 144 continues to increase as a greater concentration of drug exits catheter 14 over time. Dosage 144 may continue to increase in concentration until the concentration levels out to the concentration of drug contained in reservoir 30. Although the ramps of dosage 144 and total output dose 146 are shown as linear ramps, the percent of patient dose, or concentration, may instead be a curved ramp, exponential ramp, or any other curve representative of the concentration change of drug during delivery from IMD 12.

In some examples, the prime bolus volume and volume of mixed fluid needed to achieve a given target transition dose may be stored in memory. Table 1 provides an example of various volumes (in microliters) of fluid needed to achieve a target transition dose based on the length of catheter 14 and a specific drug (e.g., treprostinil). These examples volumes may be determined experimentally and/or extrapolated from one or more data points. Alternatively, Programmer 20 or IMD 12 may model these volumes based on known mixing factors. IMD 12 or programmer 20, for example, may use data from such a table to determine the initial delivery period required to achieve a selected target transition dose.

TABLE 1

| Target Transition Dose | Catheter Length | | |
|---|---|---|---|
| | 120 cm | 100 cm | 80 cm |
| Volume for Prime Bolus (0%) | 345 | 305 | 265 |
| 10% | 373 | 327 | 281 |
| 20% | 389 | 343 | 297 |
| 30% | 399 | 353 | 307 |
| 50% | 427 | 381 | 335 |
| 80% | 495 | 450 | 405 |

The target transition doses provided in Table 1 are the percentages of the target prescription dose delivered from IMD 12 after the prime bolus. The target transition dose is only shown as the portion from IMD 12, but 100 percent of the drug from external drug pump 26 may also be delivered to add to the total dose received by the patient. As can be seen from Table 1, a larger volume of fluid is required to achieve higher target transition doses (e.g., delivered a greater portion of the mixed fluid) and a larger volume of fluid is required to achieve the target transition doses when the catheter has a larger length. Changes to catheter diameters, type of drug, fluids containing the drug, or other factors may change the example volumes shown in Table 1.

Figure 9:
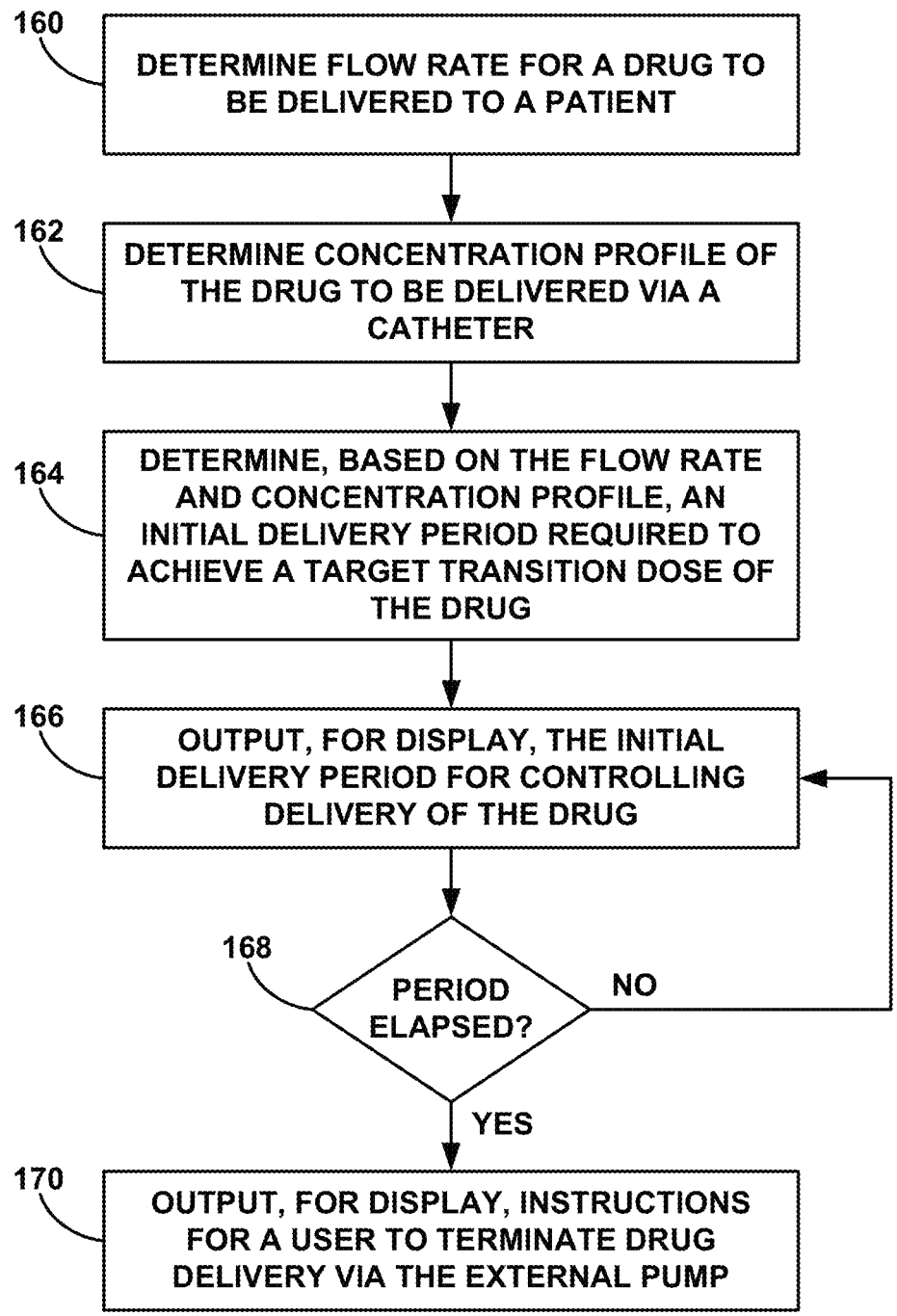
FIG. 9 is a flow diagraph of an example technique for determining an initial delivery period for transitioning drug delivery from an external drug pump to an IMD.

FIG. 9 is a flow diagram of an example process for determining an initial delivery period for transitioning drug delivery from external drug pump 26 to IMD 12. Although FIG. 9 will be described with respect to processor 50 of programmer 20, in other examples, similar techniques can also be performed by any combination of processor 34 of IMD 12, processor 80 and external drug pump 26, and/or server 110, alone or in combination with processor 50. Other sets of devices may also be used in other examples. The process of FIG. 9 may be applicable to any drug delivery transitions, such as transitions between two different drug sources. In the example of FIG. 9, the first drug source is external drug pump 26 and therapy will be transitioning to the second drug source of IMD 12. In other words, external drug pump 26 may provide a temporary delivery of one or more drugs and IMD 12 may provide a long-term or chronic source of one or more drugs for treatment of patient 1.

As shown in FIG. 9, processor 50 determines the flow rate for the drug to be delivered to patient 1 from IMD 12 (160). This flow rate is the flow rate of the new drug to be delivered from IMD 12. In some examples, processor 50 determines the flow rate by obtaining the flow rate from memory 52. For example, the flow rate may be a part of a stored therapy program 56. In addition to, or instead of, determining the flow rate based on a stored flow rate, processor 50 may determine the flow rate by receiving it from IMD 12. Processor 50 may also determine the concentration profile of the drug to be delivered via catheter 14 (162). In some examples, processor 50 determines the concentration profile from prime bolus instructions 54 of memory 52 or from IMD 12. In addition to, or instead of, obtaining the concentration profile from memory 52, processor 50 may determine the concentration profile by at least generating the concentration profile from one or more data points. For example, processor 50 may extrapolate or calculate the concentration profile based on known data points to fit the therapy parameters of patient 1. However, processor 50 may request the flow rate and/or the concentration profile from another device, such as IMD 12 in other examples.

Processor 50 may then determine, based on the obtained flow rate and concentration profile, an initial delivery period required to achieve the target transition dose of the drug (164). The initial delivery period is a duration of time (during which the drug delivery transitions from external drug pump 26 to IMD 12) required to achieve the target transition dose. Processor 50 can determine the target transition dose using any suitable technique, such as by selecting the target transition dose from memory 52 (or another memory), receiving the target transition dose from another device, or calculating the target transition dose based on stored information. Thus, in some examples, the target transition dose may be predetermined based on the type of drug and/or patient condition or selected by received user input. In accordance with the technique shown in FIG. 9, processor 50 may calculate the amount of time (i.e., the initial delivery period) that the prime bolus and portion of the mixed fluid from IMD 12 may be delivered to patient 1 until the target transition dose is reached at patient 1. At the end of the initial delivery period, the external drug pump 26 may be automatically or manually stopped such that only IMD 12 continues to deliver drug to patient 1.

In one example, processor 50 may use a formula, such as equation (1) below, to determine the initial delivery period.

$$T_{ext} = T_{prime} + \frac{V_{Ramp} - V_{prime}}{FR_{therapy}} \quad (1)$$

$T_{ext}$ is the initial delivery period that indicates when to turn off drug delivery from external drug pump 26. $T_{prime}$ is the priming period needed to move the portion of inert fluid (e.g., a priming fluid) out of catheter 14 that does not have any drug mixed with it. In other words, patient 1 would not receive any appreciable amount of drug during $T_{prime}$. $V_{ramp}$ is the total volume of mixed fluid (e.g., the mixture between the inert fluid and the fluid including the drug) needed to move out of catheter 14 to achieve the target transition dose. $V_{prime}$ is the volume of fluid in catheter 14 that does not have any drug from reservoir 30 of IMD 12. $FR_{therapy}$ is the flow rate of the drug delivery therapy to be delivered to patient 1 from IMD 12.

Processor 50 may determine the drug ramp period which indicates the time necessary for the initial portion of drug to be delivered to patient 1 in order to achieve the target transition dose. In equation (1), processor 50 determines $V_{ramp}$ from the concentration profile for the drug to be delivered and the selected target transition dose. $V_{ramp}$ may include the initial $V_{prime}$, which processor 50 may subtract from $V_{ramp}$ to identify the volume of fluid that actually includes a portion of drug. Processor 50 then divides this identified volume of fluid by $FR_{therapy}$ to calculate the drug ramp period. Alternatively, processor 50 may calculate the drug ramp period by determining the volume of delivered fluid needed to achieve the target transition dose from the concentration profile and dividing this volume of delivered fluid by the flow rate. In this manner, the volume of delivered fluid identified from the concentration profile may not include any volume of fluid without any portion of drug, such as $V_{prime}$. Processor 50 also obtains a volume of a priming fluid contained within catheter 14, wherein the volume is based on the diameter and length of the catheter 14. Processor 50 then calculates a $T_{prime}$ by dividing the volume of the priming fluid contained within catheter 14 by the flow rate. Processor 50 then calculates the initial delivery period (e.g., $T_{ext}$) by adding the drug ramp period to the priming period required to achieve the target transition dose of the drug.

In the example shown in FIG. 9, processor 50 outputs the determined initial delivery period for controlling delivery of the drug during the delivery transition of the drug to IMD 12 (166). For example, processor 50 may output the initial delivery period for display by output device 60 of programmer 20, or any other display device. In some example, outing of the initial delivery period may include processor 50 utilizing the determined initial delivery period to directly control delivery of the drug. Processor 50 may also track the initial delivery period once delivery of drug from IMD 12 has begun. If the initial delivery period has not elapsed ("NO" branch of block 168), processor 50 may continue to output the original initial delivery period, or, alternatively, the remaining portion of the initial delivery period (e.g., a countdown from the original initial delivery period). If the indicial delivery period has elapsed or expired ("YES" branch of block 168), processor 50 may output, for display at a display device such as output device 60, instructions for a user (e.g., a clinician or patient 1) to terminate drug delivery via external drug pump 26 (170). Termination of drug delivery from external drug pump 26 may include powering off external drug pump 26, stopping a pump of drug pump 26, and/or removing catheter 28 from patient 1. Alternatively, processor 50 may automatically transmit instructions to external drug pump 26 that cause processor 70 to terminate drug delivery.

The process of FIG. 9 is generally described when transitioning from and external drug pump 26 to implanted IMD 12. However, transitions between any two or more drug delivery devices may be similarly controlled. In addition, the process may be applicable for transitioning between two or more catheters of the same device. For example, the prime bolus process may be applied to transitioning from an old catheter coupled to external drug pump 26 to a new catheter (e.g., implanted more recently than the old catheter) coupled to external drug pump 26 or an old catheter coupled to IMD 12 to a new catheter coupled to IMD 12.

Figure 10A:
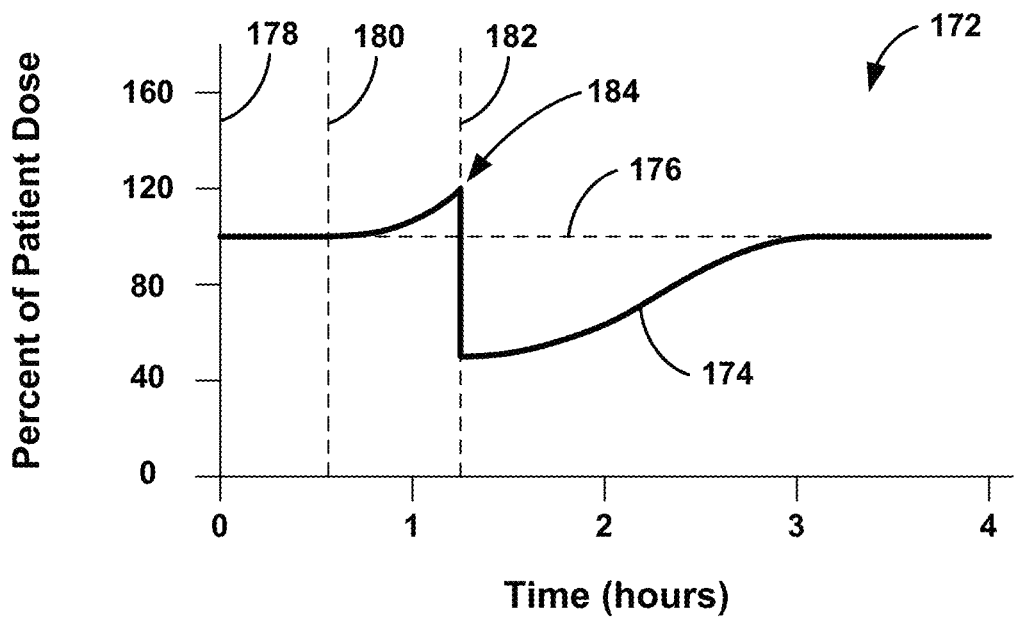
FIGS. 10A and 10B are graphs illustrating example total drug dosage delivered to a patient during a transition between different drug concentrations.
Figure 10B:
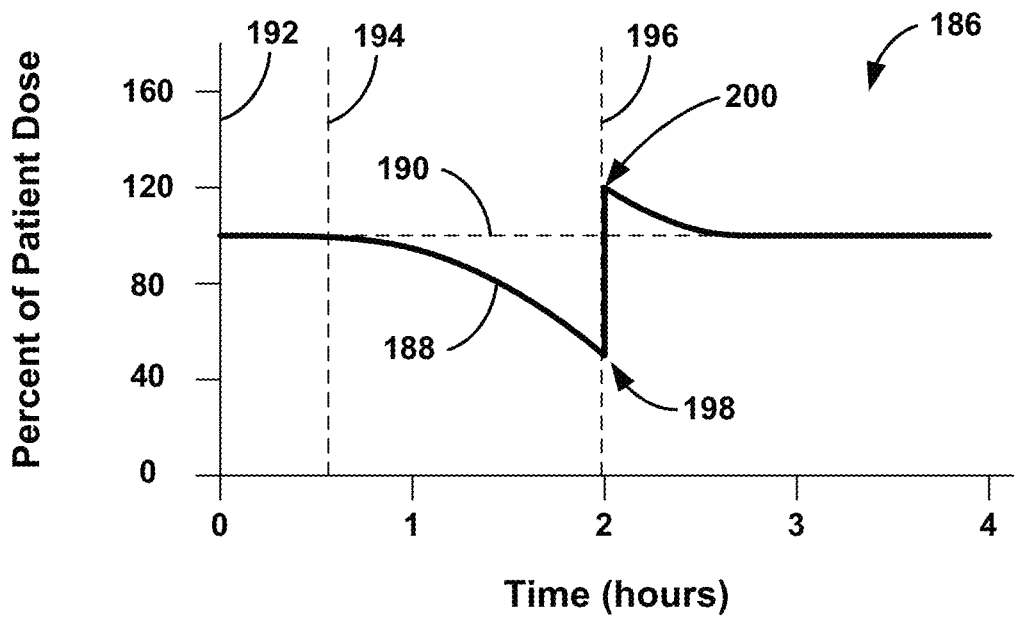

FIGS. 10A and 10B are graphs illustrating example total drug dosage delivered to a patient during a transition between different drug concentrations. The change in delivery of a drug from one concentration to a different concentration may be referred to as a bridge bolus. The bridge bolus may represent the fluid delivered to "bridge" therapy from the previous drug concentration to the new concentration. The type of transition between drug concentrations may depend on whether the new concentration (e.g., the concentration of drug refilled into reservoir 30 of IMD 12) is higher or lower than the previous concentration. For example, the timing of changing the flow rate for the new concentration can be controlled to achieve the desired target transition dose, where the target transition dose may be selected to at least one of minimize overdosing and minimize underdosing.

When transitioning between drugs of different concentrations, system 10 may also control IMD 12 to adjust the flow rate of the drug in response to expiration of the determined initial delivery period. For example, system 10 may be configured to track a duration during which the first fluid (e.g., fluid with a first concentration) is delivered to patient 1 prior to a second fluid (e.g., fluid with a second concentration) and determine that the duration exceeds the initial delivery period. If IMD 12 is refilled with a greater concentration of the drug than previously contained within the reservoir, system 10 may, responsive to determining that the duration exceeds the initial delivery period, control IMD 12 to decrease the flow rate to a second flow rate (as shown in FIG. 10A). If IMD 12 is refilled with a lesser concentration of the drug than previously contained within the reservoir, system 10 may, responsive to determining that the duration exceeds the initial delivery period, control IMD 12 to increase the flow rate to a second flow rate (as shown in FIG. 10B).

As shown by graph 172 of FIG. 10A, IMD 12 may transition drug delivery from a lower concentration to a higher concentration, such as when reservoir 30 is refilled with a higher concentration of the drug. Total dosage 174 represents the percent of the target prescribed dose that patient 1 received from IMD 12 during the transition at a given time. At time marker 178, IMD 12 first begins to pump the new, higher concentration of the drug from reservoir 30. However, the lower concentration of drug still within catheter 14 is delivered to patient 1 at the original flow rate until time marker 180 (e.g., the bridge bolus). At time marker 180, the drug from the higher concentration has mixed with the lower concentration such that the total dosage 174 begins to increase. The volume of fluid delivered between time markers 180 and 182 may be a portion of the mixed fluid. Therefore, the concentration of drug being delivered to patient 1 between time markers 180 and 182 is between the original low and high concentrations of the drug.

The period between time markers 178 and 182 represents the initial delivery period. At time marker 182, or the expiration of the initial delivery period, total dosage 176 reaches the target transition dose 184 of approximately 120 percent of the target prescribed dose 176. At time marker 182, IMD 12 reduces the flow rate to the new flow rate of the higher concentration of the drug. Total dosage 174 then immediate decreases with the lower flow rate and gradually increases again until all of the lower concentration of drug that was mixed with the higher concentration of drug is expelled from catheter 14. Therefore, at approximately three hours from time marker 178, total dosage 174 reaching 100 percent dose indicates that the concentration of drug reaching patient 1 is approximately equivalent to the concentration of drug stored within reservoir 30.

In contrast to FIG. 10A, FIG. 10B includes graph 186 in which IMD 12 may transition drug delivery from a higher concentration to a lower concentration, such as when reservoir 30 is refilled with a lower concentration of the drug. Total dosage 188 represents the percent of the target prescribed dose that patient 1 received from IMD 12 during the transition at a given time. At time marker 192, IMD 12 first begins to pump the new, lower concentration of the drug from reservoir 30. However, the higher concentration of drug still within catheter 14 is delivered to patient 1 at the original flow rate (e.g., a lower flow rate than is prescribed for the new lower concentration in reservoir 30) until time marker 194. This volume of higher concentration fluid is the bridge bolus. At time marker 194, the drug from the lower concentration has mixed with the higher concentration such that the total dosage 188 begins to decrease. The volume of fluid delivered between time markers 194 and 196 may be a portion of the mixed fluid. Therefore, the concentration of drug being delivered to patient 1 between time markers 194 and 196 is between the original high and low concentrations of the drug.

The period between time markers 192 and 196 represents the initial delivery period. At time marker 196, or the expiration of the initial delivery period, total dosage 188 reaches the target transition dose 198 of approximately 50 percent of the target prescribed dose 190. The 50 percent dose may be selected as target transition dose 198 to minimize the underdosing of drug during the transition and/or minimize the overdosing of patient 1 indicated by dose 200. At time marker 196, IMD 12 increases the flow rate to the new flow rate of the lower concentration of the drug. Total dosage 188 then immediate increases with the higher flow rate and gradually decreases again until all of the higher concentration of drug that was mixed with the lower concentration of drug is expelled from catheter 14. Therefore, at approximately 2.5 hours from time marker 192, total dosage 188 reaching 100 percent dose indicates that the concentration of drug reaching patient 1 is approximately equivalent to the concentration of drug stored within reservoir 30.

According to graphs 172 and 186, the target transition dose may be selected to balance overdosing and underdosing that may occur when switching between two different concentrations and corresponding flow rates. Using the concentration profile of a drug, the appropriate initial transition period may be selected to switch to the new flow rate of the new drug concentration before the patient is underdosed or overdosed to an adverse extent. The values of the target transition doses 184 and 198 are examples, but other target transition doses may be selected in other examples based on the type of drug, flow rates, patient condition, or any other variables. FIGS. 10A and 10B are described with respect to changing concentrations of a drug delivered by IMD 12. However, the same processes may be used to transition between concentrations of drug delivered by any implanted or external drug delivery system.

Figure 11:
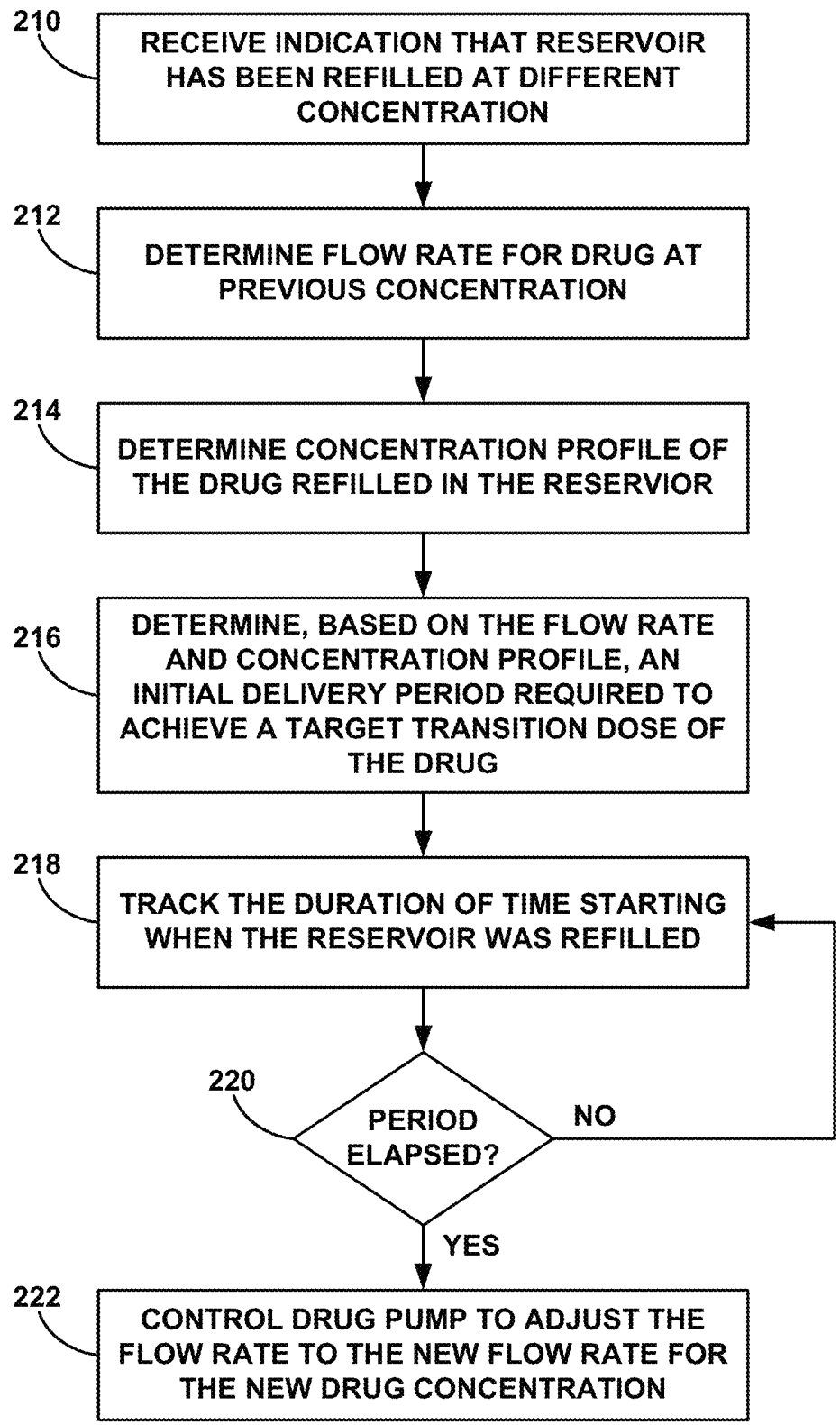
FIG. 11 is a flow diagram of an example technique for determining an initial delivery period for transitioning drug delivery between different drug concentrations.

FIG. 11 is a flow diagram of an example process for determining an initial delivery period for transitioning drug delivery between different drug concentrations. Although FIG. 11 will be described with respect to processor 34 of IMD 12, similar techniques can also be performed by any combination of processor 50 of programmer 20, processor 80 and external drug pump 26, and/or server 110, alone or in combination with processor 34. Other sets of devices may also be used in other examples. The process of FIG. 11 may be applicable to any drug delivery transitions, such as transitions between different concentrations of a drug. In the example of FIG. 11, IMD 12 may deliver a drug at a first concentration, receive a second concentration of the drug, and determine how to transition the delivery of the drug from the first concentration to the second concentration.

As shown in FIG. 11, processor 34 receives (e.g., via telemetry module 38) an indication that reservoir 30 has been refilled at a different concentration (210). This indication may be a command received from programmer 20 or a sensor that detects a change in concentration or pressure. This information indicating a change in concentration may trigger additional processes to determine when to change flow rates or otherwise switch to the delivery parameters of the new concentration of drug. Processor 34 then determines the flow rate for the drug previously delivered to patient 1 from IMD 12 (212). This flow rate is the flow rate of the previous concentration of drug in reservoir 30, or the currently delivered drug, from IMD 12. In some examples, processor 34 may determine the flow rate by, for example, obtaining the flow rate from memory 36 or programmer 20.

Processor 34 may also determine the concentration profile of the new drug concentration refilled in reservoir 30 and to be delivered via catheter 14 (214). In some examples, processor 34 may determine the concentration profile by at least obtaining the concentration profile from bridge bolus instructions in memory 36 or from programmer 20, for example. Alternatively, processor 34 may generate the concentration profile from one or more data points. For example, processor 34 may extrapolate or calculate the concentration profile based on known data points to fit the therapy parameters of patient 1. However, processor 34 may request the flow rate and/or the concentration profile from another device, such as programmer 20 or server 110 in other examples.

Processor 34 may then determine, based on the obtained flow rate and concentration profile, an initial delivery period required to achieve the target transition dose of the drug (216). The target transition dose may be predetermined based on the type of drug, the differences between the two drug concentrations, and/or patient condition or selected by received user input. In other words, processor 34 may calculate the amount of time (i.e., the initial delivery period) that the bridge bolus and portion of mixed fluid from IMD 12 may be delivered to patient 1 until the target transition dose is reached at patient 1. At the end of the initial delivery period, processor 34 may control a change in flow rate for the new drug concentration.

In one example, processor 34 may use a formula, such as equation (1) below, to calculate the initial delivery period.

$$T_{bridge} = \frac{V_{20\%}}{FR_{therapy}} \qquad (2)$$

$T_{bridge}$ is the initial delivery period that indicates when to adjust the flow rate from the old flow rate to the new flow rate. The volume of fluid delivered during $T_{bridge}$ may include the bridge bolus and a portion of the mixed fluid. $V_{20\%}$ is the total volume of fluid needed to move out of catheter 14 to achieve the target transition dose. Although the volume may be selected such that the target transition dose is 20 percent above the target prescription dose, any other target transition dose may be used to select the appropriate volume from the concentration profile of the drug. $FR_{therapy}$ is the flow rate of the drug delivery therapy for the drug concentration that was previously in reservoir 30 of IMD 12.

Processor 34 may determine $V_{20\%}$ which indicates the volume of fluid to be delivered from catheter 14 and IMD 12 (e.g., the bridge bolus and following portion of mixed fluid) to achieve the target transition dose. In equation (2), processor 20 then determines $T_{bridge}$ by dividing $V_{20\%}$ by $FR_{therapy}$. In other examples, processor 34 may separate the volumes of the bridge bolus into the volume of fluid of only the previous drug concentration and the volume of the fluid that contains both the previous and new concentration of the drug.

Processor 34 may then track the duration of time starting when reservoir 30 was refilled for the time that drug was pumped to patient 1 (218). For example, processor 34 can include a clock or a counter. This duration of time that is tracked is compared to the initial delivery period. If the initial delivery period has not elapsed ("NO" branch of block 220), processor 34 may continue to track the duration of time that has elapsed (218). If the initial delivery period has elapsed or expired ("YES" branch of block 220), processor 34 controls medical pump 40 to adjust the flow rate to the new flow rate for the new drug concentration (222). At this time, the output dose of drug to patient 1 may be at the target transition dose. As described herein, processor 34 may increase the flow rate when transitioning from a higher concentration to a lower concentration of the drug. Alternatively, processor 34 may decrease the flow rate when transition from a lower concentration to a higher concentration.

The process of FIG. 11 is generally described when transitioning to a different concentration of drug for drug delivery therapy from IMD 12. However, these processes may be applied to the transition between different drug concentrations for any implanted or external drug delivery devices. In other words, the devices herein may determine when to adjust a flow rate of drug delivery to accommodate the change in drug concentration.

As described above, in some examples, system 10 can be configured to generate and present, e.g., via user interface 58 of programmer 20, information related to a transition of drug delivery from one device to another, from one drug to another drug, from one drug concentration to another drug concentration, or another drug delivery transition. In some examples, system 10 is configured to generate and present a graphical user interface with which a user may interact to control a drug delivery transition.

Figure 12:
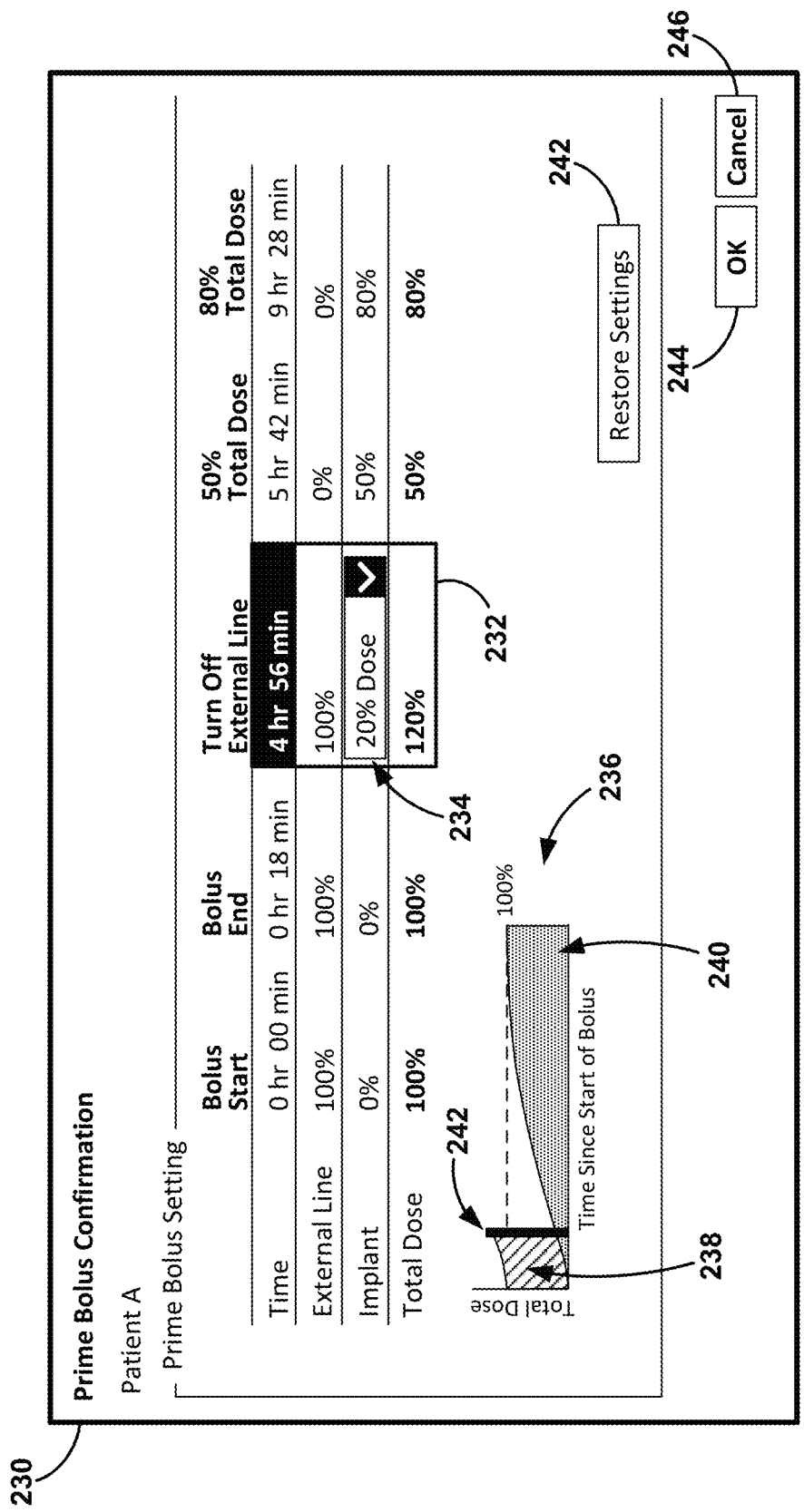
FIG. 12 is a conceptual diagram of an example user interface that presents information relating to transitioning drug delivery from an external drug pump to an IMD.

FIG. 12 is a conceptual diagram of example graphical user interface 230 that presents information relating to transitioning drug delivery from external drug pump 26 to IMD 12. The example of user interface 230 is directed to the transition of sources for the therapeutic fluid treprostinil, which may be delivered to the heart of patient 1 in order to treat symptoms related to pulmonary arterial hypertension (PAH). However, user interface 230 may be configured for use with any type of therapeutic fluid, agent or drug, as described herein.

User interface 230 may be generate and presented by one or more of programmer 20, external drug pump 26, or any other computing device comprising a display device. Programmer 20 will be described for the purposes of FIG. 12. User interface 230 presents several items of information to a user regarding the delivery of drug therapy and may also provide one or more fields that receive input from a user. As shown in FIG. 12, user interface 230 includes dosage output graph 236, target transition dose field 232, restore settings button 242, OK button 244, and cancel button 246.

User interface 230 also provides various time events in the form of text and/or numbers for the course of transitioning drug delivery from external drug pump 26 (e.g., the "External Line") to IMD 12 (e.g., the "Implant"). The category "Bolus Start" indicates the initial time at which IMD 12 begins to pump fluid from catheter 14. The category "Bolus End" indicates the time at which a portion of the drug from reservoir 30 begins to exit catheter 14 and reach patient 1. Which, at this time, the implant dosage still indicates "0%" because no drug has yet exited catheter 14. The "Turn Off External Line" category indicates the end of the initial delivery period, where the combination of dosage from the External Line and the Implant equals the target transition dose represented in target transition dose field 232 by target transition dose input 234.

Target transition dose input 234 is shown as a drop down menu with which a user may select from one or more different dosages (e.g., 0%, 10%, 20%, 30%, 50%, etc.). In other examples, target transition dose input 234 may include a text field that accepts user input in the form of any number or text describing the desired target transition dose, a link to another screen or pop-up screen that accepts user input selecting a target transition dose, or any other forms of user input. In this manner, the user input received via target transition dose input 234 may define the target transition dose used to calculate the initial delivery period. In some examples, the target transition dose input may be preselected by programmer 20 based on the type of drug, the patient condition, or any other factors. In one example, user interface 230 may present a warning notification to the user in response to receiving a user input change to the target transition dose.

After the user has selected the desired target transition dose, processor 50 of programmer 20 (or another device) may calculate the initial delivery period as described herein. Target transition dose field 232 indicates the calculated initial delivery period as "4 hr 56 min" in the example of FIG. 12. Target transition dose field 232 may be bolded, presented with a unique color, or have some other indication to clearly identify the calculated initial delivery period. Processor 50 can update the initial delivery period presented via user interface 230 in order to count down the time remaining in the initial delivery period in real-time during delivery of drug, or user interface 230 generated by processor 50 can include another timer that provides the time remaining from the initial delivery period until the external drug pump 26 should be turned off. This is one example manner in which processor 50 may output an initial delivery period (166), as described with respect to FIG. 9.

User interface 230 may also include additional categories to indicate the dosage the patient is receiving after the External Line has been turned off. For example, the category "50% Total Dose" indicates the time at which patient 1 would be receiving 50 percent of the target prescribed dose. The category "80% Total Dose" indicates the time at which patient 1 would be receiving 80 percent of the target prescribed dose. Processor 50 of programmer 20 (or another device) may calculate these total dosages based on the target transition dose, the concentration profile of the drug, and/or the flow rate of the drug when delivered from IMD 12. Since patient 1 will be underdosed during this period, the user may update the desired target transition dose, via target transition dose input 234, in order to balance potential overdosing and underdosing during the transition from external drug pump 26 to IMD 12.

Dosage output graph 236 may graphically represent the total output dosage during the transition from each contributing drug source. Dosage output graph 236 includes first dosing portion 238, second dosing portion 240, and delivery change 242. First dosing portion 238 represents the drug dose delivered to patient 1 from external drug pump 26. Second dosing portion 240 represents the drug dose delivered to patient 1 from IMD 12. When combined, dosage output graph 236 illustrates the total output dosage of the drug received by the patient over time and the respective portions of drug being received from each of the drug sources. In other words, the areas under each of first dosing portion 238 and second doing portion 240 may be stacked on top of each other to represent the total output dosage.

Each of first dosing portion 238 and second dosing portion 240 may be visually different, such as represented by different colors, patterns, shading, or any other differentiating visual indication. The visual distinction between first dosing portion 238 and second dosing portion 240 may also be matched (e.g., with a common coding scheme) with the respective textual information presented above dosage output graph 236. For example, first dosing portion 238 and the text of the "External Line" row may both be presented in the color red, whereas second dosing portion 240 and the text of the "Implant" row may be both presented in the color blue. In this case, user interface 230 presents a clear correlation between which information is related to which respective drug delivery source. Furthermore, no legend may be required when color coding or otherwise visually matching graphical and textual information.

Delivery change 242 graphically represents the time at which the initial delivery period expires and there is a change to the delivery sources, such as turning off the external line from external drug pump 26. In some examples, user interface 230 may update dosage output graph 236 during the drug transition to show a real-time marker representing the current time and dosage being delivered to patient 1. This real-time marker may be a moving bar or arrow that moves with time across dosage output graph 236.

Restore settings button 242 may be selected by a user to revert all of the inputs and information received by the user to the default information. For example, programmer 20 may, after receiving input via restore setting button 242, change the target transition dose back to the default target transition dose and recalculate the related times. Programmer 20 may save the settings shown in user interface 230 and begin the transition of drug in response to receiving selection of OK button 244. Programmer 20 may exit the current screen and return to a previous menu in response to receiving selection of Cancel button 246.

Although user interface 230 is described with respect to transitioning between two different drug sources, user interface 230 may be modified to present information related to the transition between different drug concentrations as well. For example, user interface 230 may receive the target transition dose, present textual information indicating the times of various events during the transition (e.g., the initial delivery period and various total output doses), and a graph indicating the total output dose patient 1 would receive over time during the transition. This graph may be similar to graphs 172 and 186 of FIGS. 10A and 10B, respectively.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to IMD 12, programmer 20, external drug pump 26, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. For example, any of the techniques or processes described herein may be performed within one device or at least partially distributed amongst two or more devices, such as between programmer 20, IMD 12, and/or external drug pump 26. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A method comprising:
   determining a flow rate for a fluid to be delivered to a patient via a drug pump and a catheter in fluid communication with a reservoir of the drug pump, wherein the fluid comprises a therapeutic agent;
   determining a concentration profile of the therapeutic agent delivered via the catheter, wherein the concentration profile represents a gradient of different concentrations of the therapeutic agent along a length of the catheter and identifies a volume of the fluid deliverable by the drug pump and needed to achieve a target transition dose of the therapeutic agent; and
   determining, by a processor and based on the flow rate and the concentration profile, an initial delivery period required to achieve the target transition dose by delivering the fluid at the flow rate.

2. The method of claim 1, wherein the fluid is a first fluid, wherein the volume of the fluid is a first volume of the first fluid, and wherein determining the initial delivery period further comprises:
   calculating a drug ramp period by dividing the first volume of the first fluid deliverable by the drug pump and needed to achieve the target transition dose of the therapeutic agent by the flow rate;
   determining a second volume of a priming fluid different from the first fluid and contained within the catheter, wherein the second volume is based on a diameter and the length of the catheter;
   calculating a priming period by dividing the second volume of the priming fluid contained within the catheter by the flow rate; and
   adding the priming period to the drug ramp period to determine the initial delivery period required to achieve the target transition dose of the therapeutic agent.

3. The method of claim 1, wherein the fluid is a first fluid, further comprising:
   tracking a duration during which the first fluid is delivered to the patient by the drug pump;
   determining that the duration exceeds the initial delivery period; and
   responsive to determining that the duration exceeds the initial delivery period, displaying an instruction for a user to terminate delivery of a second fluid from an external drug delivery pump.

4. The method of claim 1, wherein the flow rate is a first flow rate, further comprising:
   tracking a duration during which the fluid is delivered;
   determining that the duration exceeds the initial delivery period; and
   responsive to determining that the duration exceeds the initial delivery period, controlling the drug pump to increase the first flow rate to a second flow rate, wherein a first concentration of the therapeutic agent contained in the reservoir is less than a second concentration of the therapeutic agent delivered to the patient prior to the first concentration.

5. The method of claim 1, wherein the flow rate is a first flow rate, further comprising:
   tracking a duration during which the fluid is delivered;
   determining that the duration exceeds the initial delivery period; and
   responsive to determining that the duration exceeds the initial delivery period, controlling the drug pump to decrease the flow rate to a second flow rate, wherein a first concentration of the therapeutic agent contained in the reservoir is greater than a second concentration of the therapeutic agent delivered to the patient prior to the first concentration.

6. The method of claim 1, wherein the target transition dose of the therapeutic agent is different than a target prescribed dose of the therapeutic agent, and wherein a transition concentration of the therapeutic agent within the fluid during the initial delivery period is different than a reservoir concentration of the therapeutic agent stored within the reservoir.

7. The method of claim 1, wherein the concentration profile is based on diffusion of the therapeutic agent within the fluid of the catheter.

8. The method of claim 1, further comprising outputting, for presentation at a display device, a graph of a total output dose of the therapeutic agent delivered to the patient with respect to time, a representation of the target transition dose with respect to the total output dose, and an indication of the initial delivery period.

9. The method of claim 8, wherein outputting the graph further comprises:
   outputting, for presentation at the display, a first dosing portion representing dosing of the therapeutic agent delivered from the reservoir of the drug pump, wherein an implantable medical device comprises the drug pump; and
   outputting, for presentation at the display, a second dosing portion representing dosing from the therapeutic agent delivered from an external drug delivery pump, wherein a sum of the first dosing portion and the second dosing portion represents the total output dose.

10. The method of claim 1, further comprising receiving, via a user interface, user input defining the target transition dose of the therapeutic agent.

11. The method of claim 1, wherein one of an external programmer or a device comprising the drug pump comprises the processor.

12. A system comprising:
   one or more processors configured to:
      determine a flow rate for a fluid to be delivered to a patient via a drug pump and a catheter in fluid communication with a reservoir of the drug pump, wherein the fluid comprises a therapeutic agent;
      determine a concentration profile of the therapeutic agent delivered via the catheter, wherein the concentration profile represents a gradient of different concentrations of the therapeutic agent along a length of the catheter and identifies a volume of the fluid deliverable by the drug pump and needed to achieve a target transition dose of the therapeutic agent; and
      determine, based on the flow rate and the concentration profile, an initial delivery period required to achieve the target transition dose by delivering the fluid at the flow rate.

13. The system of claim 12, wherein the fluid is a first fluid, wherein the volume of the fluid is a first volume of the first fluid, and wherein, to determine the initial delivery period, the one or more processors are configured to:
   calculate a drug ramp period by dividing the first volume of the first fluid deliverable by the drug pump and needed to achieve the target transition dose of the therapeutic agent by the flow rate;
   determine a second volume of a priming fluid different from the first fluid contained within the catheter, wherein the second volume is based on a diameter and the length of the catheter;
   calculate a priming period by dividing the second volume of the priming fluid contained within the catheter by the flow rate; and
   add the priming period to the drug ramp period to determine the initial delivery period required to achieve the target transition dose of the therapeutic agent.

14. The system of claim 12, wherein the fluid is a first fluid, and wherein the one or more processors are configured to:
   track a duration during which the first fluid is delivered to the patient by the drug pump;
   determine that the duration exceeds the initial delivery period; and
   responsive to determining that the duration exceeds the initial delivery period, output, for display via a display device, an instruction for a user to terminate delivery of a second fluid from an external drug delivery pump.

15. The system of claim 12, wherein the flow rate is a first flow rate, and wherein the one or more processors are configured to:
   track a duration during which the fluid is delivered;
   determine that the duration exceeds the initial delivery period; and
   responsive to determining that the duration exceeds the initial delivery period, control the drug pump to increase the first flow rate to a second flow rate, wherein a first concentration of the therapeutic agent contained in the reservoir is less than a second concentration of the therapeutic agent delivered to the patient prior to the first concentration.

16. The system of claim 12, wherein the flow rate is a first flow rate, and wherein the one or more processors are configured to:
   track a duration during which the fluid is delivered;
   determine that the duration exceeds the initial delivery period; and
   responsive to determining that the duration exceeds the initial delivery period, control the drug pump to decrease the flow rate to a second flow rate, wherein a first concentration of the therapeutic agent contained in the reservoir is greater than a second concentration of the therapeutic agent delivered to the patient prior to the first concentration.

17. The system of claim 12, wherein the target transition dose of the therapeutic agent is different than a target prescribed dose of the therapeutic agent, and wherein a transition concentration of the therapeutic agent within the fluid during the initial delivery period is different than a reservoir concentration of the therapeutic agent stored within the reservoir.

18. The system of claim 12, wherein the concentration profile is based on diffusion of the therapeutic agent within the fluid of the catheter.

19. The system of claim 12, further comprising a display device, wherein the one or more processors are configured to output, for presentation at the display device, a graph of a total output dose of the therapeutic agent delivered to the patient with respect to time, a representation of the target transition dose with respect to the total output dose, and an indication of the initial delivery period.

20. The system of claim 19, wherein, to output the graph, the one or more processors are further configured to:
output, for presentation at the display, a first dosing portion representing dosing of the therapeutic agent delivered via the reservoir of the drug pump, wherein an implantable medical device comprises the drug pump; and
output, for presentation at the display, a second dosing portion representing dosing from the therapeutic agent delivered from an external drug delivery pump, wherein a sum of the first dose portion and the second dose portion represents the total output dose.

21. The system of claim 12, further comprising a user interface configured to receive user input defining the target transition dose of the therapeutic agent.

22. The system of claim 12, wherein the system comprises an implantable medical device, and wherein the implantable medical device comprises the drug pump.

23. The system of claim 12, wherein the system comprises an external programmer configured to control the drug pump.

24. A system comprising:
means for determining a flow rate for a fluid to be delivered to a patient via a drug pump and a catheter in fluid communication with a reservoir of the drug pump, wherein the fluid comprises a therapeutic agent;
means for determining a concentration profile of the therapeutic agent delivered via the catheter, wherein the concentration profile represents a gradient of different concentrations of the therapeutic agent along a length of the catheter and identifies a volume of the fluid deliverable by the drug pump and needed to achieve a target transition dose of the therapeutic agent; and
means for determining, based on the flow rate and the concentration profile, an initial delivery period required to achieve the target transition dose by delivering the fluid at the flow rate.

\* \* \* \* \*